United States Patent
Okoniewski et al.

(10) Patent No.: US 11,832,849 B2
(45) Date of Patent: *Dec. 5, 2023

(54) SURGICAL ACCESS DEVICE

(71) Applicant: Covidien LP, Mansfield, MA (US)

(72) Inventors: Gregory Okoniewski, North Haven, CT (US); Nizamudheen Kalakkudi Chalil, Calicut (IN); Jay Breindel, Kensington, CT (US); Christopher K. Evans, Southington, CT (US); Brandon Lee Calavan, Windsor, CT (US)

(73) Assignee: COVIDIEN LP, Mansfield, MA (US)

( * ) Notice: Subject to any disclaimer, the term of this patent is extended or adjusted under 35 U.S.C. 154(b) by 1026 days.

This patent is subject to a terminal disclaimer.

(21) Appl. No.: 16/713,320

(22) Filed: Dec. 13, 2019

(65) Prior Publication Data

US 2020/0113601 A1    Apr. 16, 2020

Related U.S. Application Data

(63) Continuation of application No. 15/573,661, filed as application No. PCT/US2016/031711 on May 11, 2016, now Pat. No. 10,543,018.
(Continued)

(51) Int. Cl.
*A61B 17/34* (2006.01)
*A61B 17/02* (2006.01)
(Continued)

(52) U.S. Cl.
CPC ...... *A61B 17/3498* (2013.01); *A61B 17/0218* (2013.01); *A61B 17/3423* (2013.01);
(Continued)

(58) Field of Classification Search
CPC ............ A61B 17/0218; A61B 17/3423; A61B 17/3462; A61B 17/3498; A61B 17/3474; A61B 2017/3464
See application file for complete search history.

(56) References Cited

U.S. PATENT DOCUMENTS 448,702 A    3/1891  Wilson
3,504,699 A  4/1970  Grise
(Continued)

FOREIGN PATENT DOCUMENTS

CN    102580233 A     7/2012
DE    202008009527 U1 10/2008
(Continued)

OTHER PUBLICATIONS

European Search Report dated Jan. 17, 2019, issued in EP Appln. No. 16796950.
(Continued)

*Primary Examiner* — Lynnsy M Summitt
(74) *Attorney, Agent, or Firm* — Carter, DeLuca & Farrell LLP

(57) ABSTRACT

A valve assembly for use with a surgical instrument is disclosed. The valve assembly includes a housing and a seal assembly disposed within the housing, the seal assembly including a septum seal including an orifice configured to sealingly engage a surgical instrument inserted therethrough, at least a portion of the septum seal defining a seal curvature, a first guard member including a plurality of curved first guard portions defining slits therebetween, and a second guard member including a plurality of curved second guard portions defining slits therebetween. The first and second guard members may be positioned in an overlapping relationship with the plurality of first guard portions rotationally offset with respect to the second guard portions. The wide, triangular shaped slits of the guard members may improve flexibility of the guard portions.

20 Claims, 40 Drawing Sheets

Related U.S. Application Data

(60) Provisional application No. 62/161,930, filed on May 15, 2015.

(51) Int. Cl.
  *A61B 17/00* (2006.01)
  *A61B 90/00* (2016.01)
  *A61B 17/32* (2006.01)

(52) U.S. Cl.
  CPC ...... *A61B 17/3462* (2013.01); *A61B 17/3474* (2013.01); *A61B 90/37* (2016.02); *A61B 2017/00477* (2013.01); *A61B 2017/00907* (2013.01); *A61B 2017/00955* (2013.01); *A61B 2017/320044* (2013.01); *A61B 2017/3454* (2013.01); *A61B 2017/3456* (2013.01); *A61B 2017/3464* (2013.01)

(56) References Cited

U.S. PATENT DOCUMENTS

| | | |
|---|---|---|
| 3,773,233 A | 11/1973 | Souza |
| 4,436,519 A | 3/1984 | O'Neill |
| 4,601,710 A | 7/1986 | Moll |
| 4,610,665 A | 9/1986 | Matsumoto et al. |
| 4,654,030 A | 3/1987 | Moll et al. |
| 4,902,280 A | 2/1990 | Lander |
| 4,931,042 A | 6/1990 | Holmes et al. |
| 4,932,633 A | 6/1990 | Johnson et al. |
| 5,030,206 A | 7/1991 | Lander |
| 5,053,013 A | 10/1991 | Ensminger et al. |
| 5,098,388 A | 3/1992 | Kulkashi et al. |
| 5,104,383 A | 4/1992 | Shichman |
| 5,203,773 A | 4/1993 | Green |
| 5,209,737 A | 5/1993 | Ritchart et al. |
| 5,211,634 A | 5/1993 | Vaillancourt |
| 5,246,425 A | 9/1993 | Hunsberger et al. |
| 5,300,033 A | 4/1994 | Miller |
| 5,308,336 A | 5/1994 | Hart et al. |
| 5,324,270 A | 6/1994 | Kayan et al. |
| 5,342,315 A | 8/1994 | Rowe et al. |
| 5,343,775 A | 9/1994 | Easton et al. |
| 5,366,445 A | 11/1994 | Haber et al. |
| 5,385,552 A | 1/1995 | Haber et al. |
| 5,385,553 A | 1/1995 | Hart et al. |
| 5,441,041 A | 8/1995 | Sauer et al. |
| 5,456,284 A | 10/1995 | Ryan et al. |
| 5,467,762 A | 11/1995 | Sauer et al. |
| 5,534,009 A | 7/1996 | Lander |
| 5,542,931 A | 8/1996 | Gravener et al. |
| 5,549,565 A | 8/1996 | Ryan et al. |
| 5,569,160 A | 10/1996 | Sauer et al. |
| 5,578,016 A | 11/1996 | Zinger |
| 5,584,850 A | 12/1996 | Hart et al. |
| 5,603,702 A | 2/1997 | Smith et al. |
| 5,628,732 A | 5/1997 | Antoon, Jr. et al. |
| 5,643,301 A | 7/1997 | Mollenauer |
| 5,657,963 A | 8/1997 | Hinchliffe et al. |
| 5,720,730 A | 2/1998 | Blake, III |
| 5,725,504 A | 3/1998 | Collins |
| 5,743,884 A | 4/1998 | Hasson et al. |
| 5,752,938 A | 5/1998 | Flatland et al. |
| 5,800,451 A | 9/1998 | Buess et al. |
| 5,807,338 A | 9/1998 | Smith et al. |
| 5,871,471 A | 2/1999 | Ryan et al. |
| 5,895,377 A | 4/1999 | Smith et al. |
| 5,980,493 A | 11/1999 | Smith et al. |
| 6,024,729 A | 2/2000 | Dehdashtian et al. |
| 6,080,134 A | 6/2000 | Lotti et al. |
| 6,086,603 A | 7/2000 | Termin et al. |
| 6,093,176 A | 7/2000 | Dennis |
| 6,170,785 B1 | 1/2001 | Lampropoulos et al. |
| 6,254,529 B1 | 7/2001 | Ouchi |
| 6,270,484 B1 | 8/2001 | Yoon |
| 6,277,100 B1 | 8/2001 | Raulerson et al. |
| 6,302,852 B1 | 10/2001 | Fleming, III et al. |
| 6,352,520 B1 | 3/2002 | Miyazaki |
| 6,569,120 B1 | 5/2003 | Green et al. |
| 6,613,063 B1 | 9/2003 | Hunsberger |
| 6,685,630 B2 | 2/2004 | Sauer et al. |
| 6,702,787 B2 | 3/2004 | Racenet et al. |
| 6,981,966 B2 | 1/2006 | Green |
| 7,344,519 B2 | 3/2008 | Wing et al. |
| 7,654,735 B2 | 2/2010 | Sisk et al. |
| 7,731,692 B2 | 6/2010 | Moos et al. |
| 7,828,773 B2 | 11/2010 | Swisher et al. |
| 7,850,650 B2 | 12/2010 | Breitweiser |
| 7,905,857 B2 | 3/2011 | Swisher |
| 7,976,498 B2 | 7/2011 | Swisher et al. |
| 7,981,092 B2 | 7/2011 | Duke |
| 8,012,128 B2 | 9/2011 | Franer et al. |
| 8,092,431 B2 | 1/2012 | Lunn et al. |
| 8,109,910 B2 | 2/2012 | Zastawny et al. |
| 8,147,457 B2 | 4/2012 | Michael et al. |
| 8,162,889 B2 | 4/2012 | Swisher et al. |
| 8,273,060 B2 | 9/2012 | Moreno, Jr. et al. |
| 8,348,894 B2 | 1/2013 | Swisher et al. |
| 8,353,874 B2 | 1/2013 | Okoniewski |
| 8,357,104 B2 | 1/2013 | Moos et al. |
| 8,377,090 B2 | 2/2013 | Taylor et al. |
| 8,419,687 B2 | 4/2013 | Moos et al. |
| 8,430,851 B2 | 4/2013 | McGinley et al. |
| 8,449,460 B2 | 5/2013 | Duke et al. |
| 8,491,533 B2 | 7/2013 | Parihar et al. |
| 8,517,977 B2 | 8/2013 | Taylor et al. |
| 8,523,809 B2 | 9/2013 | Moos et al. |
| 8,568,362 B2 | 10/2013 | Moreno, Jr. et al. |
| 8,579,807 B2 | 11/2013 | Moreno, Jr. et al. |
| 8,608,768 B2 | 12/2013 | Taylor et al. |
| 8,636,686 B2 | 1/2014 | Minnelli et al. |
| 8,636,759 B2 | 1/2014 | Pingleton et al. |
| D700,326 S | 2/2014 | Minnelli et al. |
| 8,690,831 B2 | 4/2014 | Duke |
| 8,740,925 B2 | 6/2014 | Bettuchi et al. |
| 8,821,526 B2 | 9/2014 | Winfree et al. |
| 8,834,417 B2 | 9/2014 | Moos et al. |
| 8,870,747 B2 | 10/2014 | Moreno, Jr. et al. |
| 8,915,842 B2 | 12/2014 | Weisenburgh, II et al. |
| 8,932,249 B2 | 1/2015 | Parihar et al. |
| 8,968,250 B2 | 3/2015 | McGinley et al. |
| 9,033,929 B2 | 5/2015 | Moreno et al. |
| D735,852 S | 8/2015 | Minnelli et al. |
| D736,926 S | 8/2015 | Minnelli et al. |
| 9,101,315 B2 | 8/2015 | Winfree et al. |
| 9,155,558 B2 | 10/2015 | Albrecht et al. |
| 9,186,173 B2 | 11/2015 | Winfree et al. |
| 9,254,148 B2 | 2/2016 | Hart |
| 9,265,899 B2 | 2/2016 | Albrecht et al. |
| 9,339,292 B2 | 5/2016 | Poore et al. |
| 9,358,041 B2 | 6/2016 | Moreno, Jr. et al. |
| 9,545,248 B2 | 1/2017 | Taylor et al. |
| 9,545,264 B2 | 1/2017 | Mastri et al. |
| 9,788,857 B2 | 10/2017 | Bettuchi et al. |
| 10,543,018 B2 * | 1/2020 | Okoniewski ....... A61B 17/3462 |
| 2002/0007153 A1 | 1/2002 | Wells et al. |
| 2002/0010425 A1 | 1/2002 | Guo et al. |
| 2003/0195472 A1 | 10/2003 | Green et al. |
| 2004/0049173 A1 | 3/2004 | White et al. |
| 2004/0064100 A1 | 4/2004 | Smith |
| 2004/0147949 A1 | 7/2004 | Stellon et al. |
| 2004/0171990 A1 | 9/2004 | Dennis et al. |
| 2005/0096605 A1 | 5/2005 | Green et al. |
| 2006/0264992 A1 | 11/2006 | Franer et al. |
| 2006/0291755 A1 | 12/2006 | Olin et al. |
| 2007/0073240 A1 | 3/2007 | Moos et al. |
| 2008/0086074 A1 | 4/2008 | Taylor et al. |
| 2008/0161758 A1 | 7/2008 | Insignares |
| 2008/0300545 A1 | 12/2008 | Hsieh |
| 2009/0093682 A1 | 4/2009 | Izzo et al. |
| 2009/0192444 A1 | 7/2009 | Albrecht et al. |
| 2009/0209915 A1 | 8/2009 | Zastawny et al. |
| 2009/0270681 A1 | 10/2009 | Moreno et al. |
| 2009/0270817 A1 | 10/2009 | Moreno et al. |
| 2010/0010310 A1 | 1/2010 | Weisenburgh, II et al. |

(56) References Cited

U.S. PATENT DOCUMENTS

| | | |
|---|---|---|
| 2010/0022958 A1 | 1/2010 | Moreno, Jr. et al. |
| 2010/0094228 A1 | 4/2010 | Bettuchi et al. |
| 2010/0114033 A1 | 5/2010 | Fischvogt |
| 2010/0160938 A9 | 6/2010 | Franer et al. |
| 2010/0234688 A1 | 9/2010 | Carter |
| 2010/0331625 A1 | 12/2010 | Rosemurgy et al. |
| 2011/0087159 A1 | 4/2011 | Parihar et al. |
| 2011/0087169 A1 | 4/2011 | Parihar et al. |
| 2011/0202008 A1 | 8/2011 | Okoniewski |
| 2011/0301411 A1 | 12/2011 | Brannon |
| 2014/0277056 A1 | 9/2014 | Poore et al. |
| 2015/0038797 A1 | 2/2015 | Furnish |
| 2015/0123355 A1 | 5/2015 | Castro et al. |
| 2016/0228139 A1 | 8/2016 | Poore et al. |

FOREIGN PATENT DOCUMENTS

| | | |
|---|---|---|
| EP | 2174603 A1 | 4/2010 |
| JP | H0663156 A | 3/1994 |
| JP | 2009534085 A | 9/2009 |

OTHER PUBLICATIONS

Japanese Office Action dated May 22, 2020, issued in JP Appln. No. 2017559409.

* cited by examiner

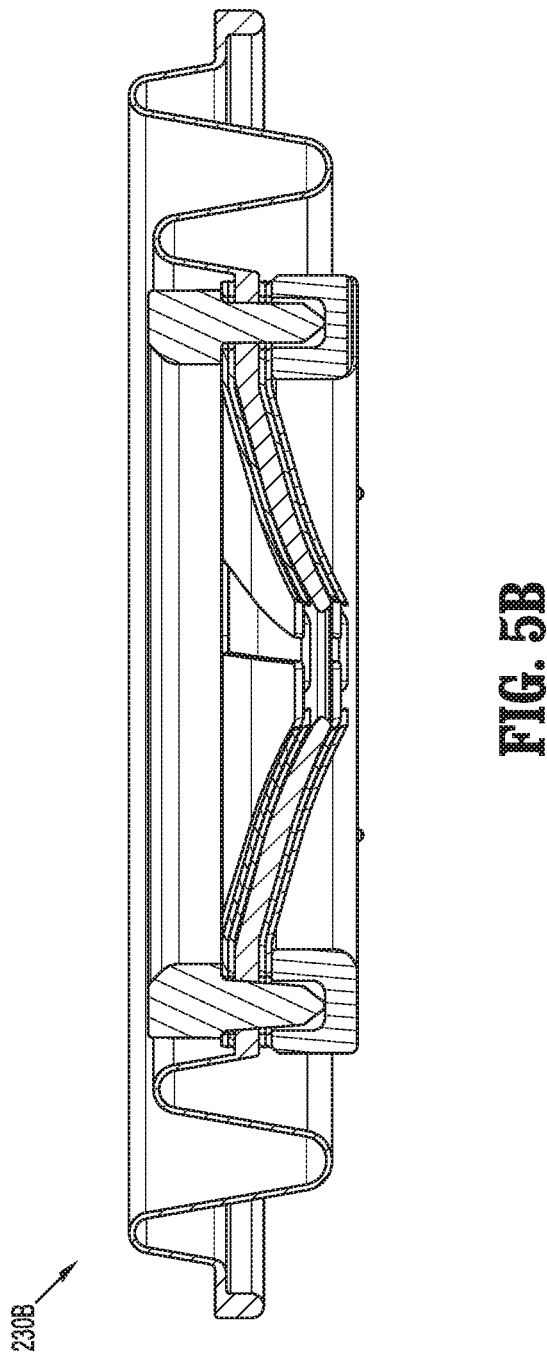

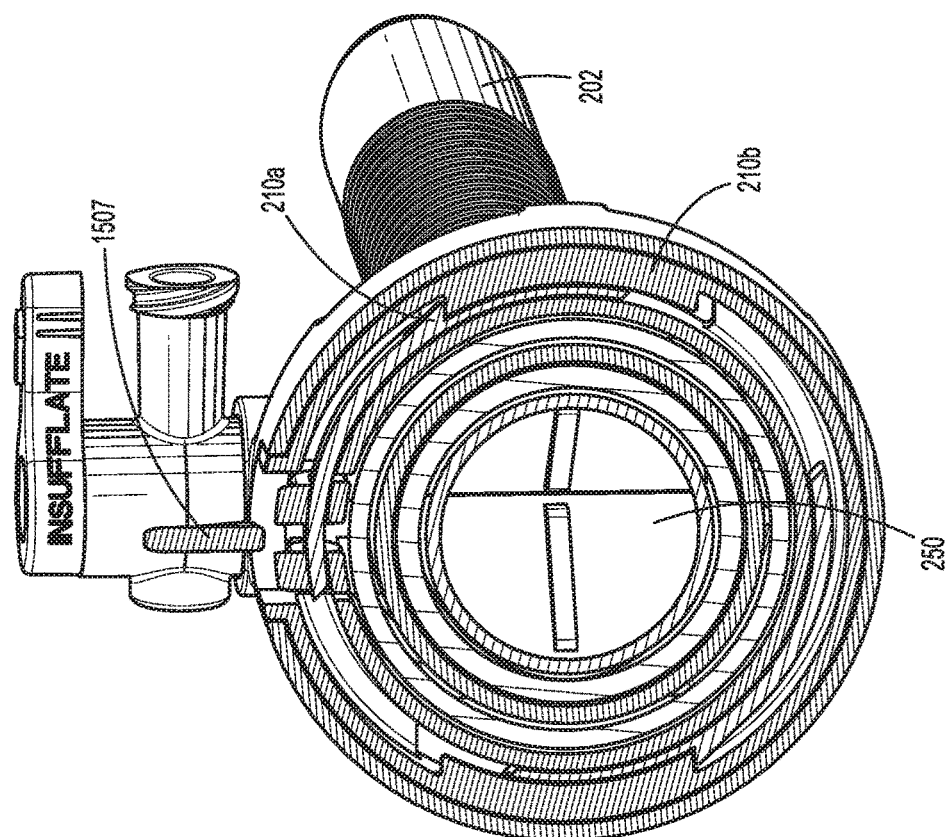
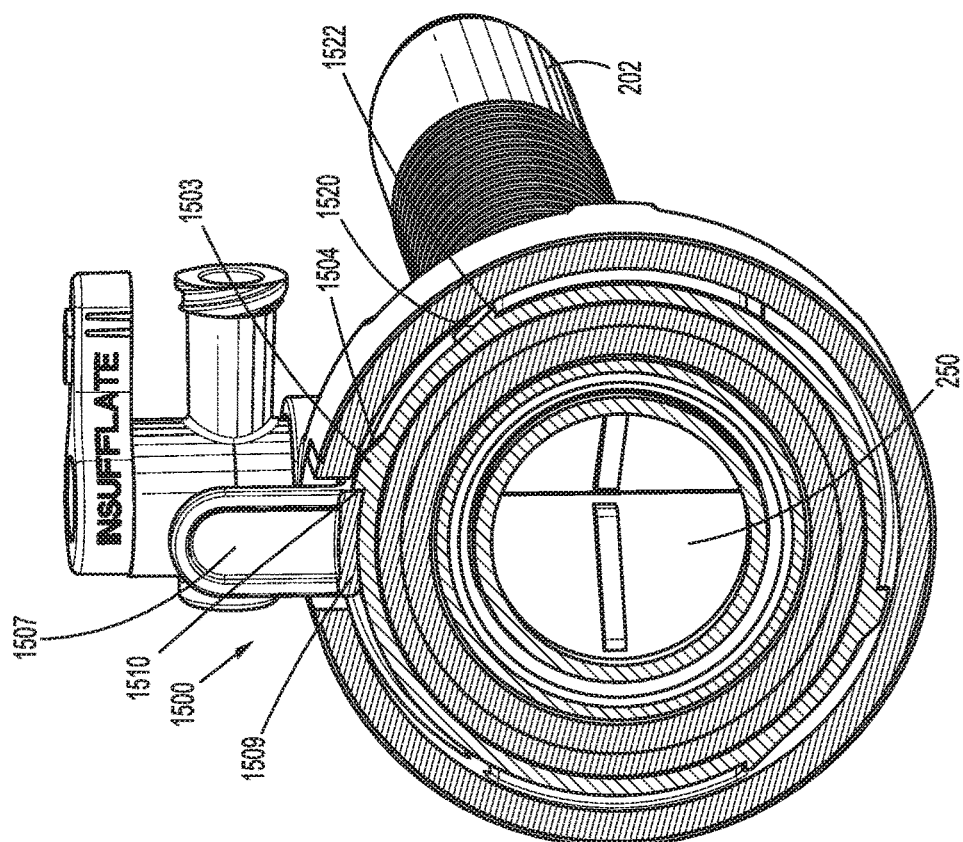
FIG. 11
FIG. 12

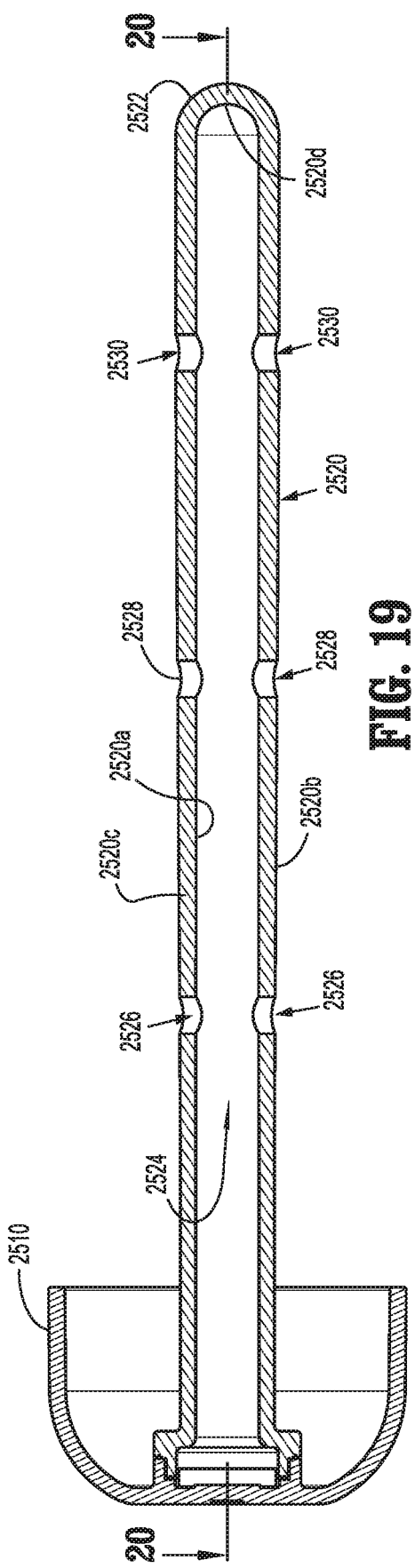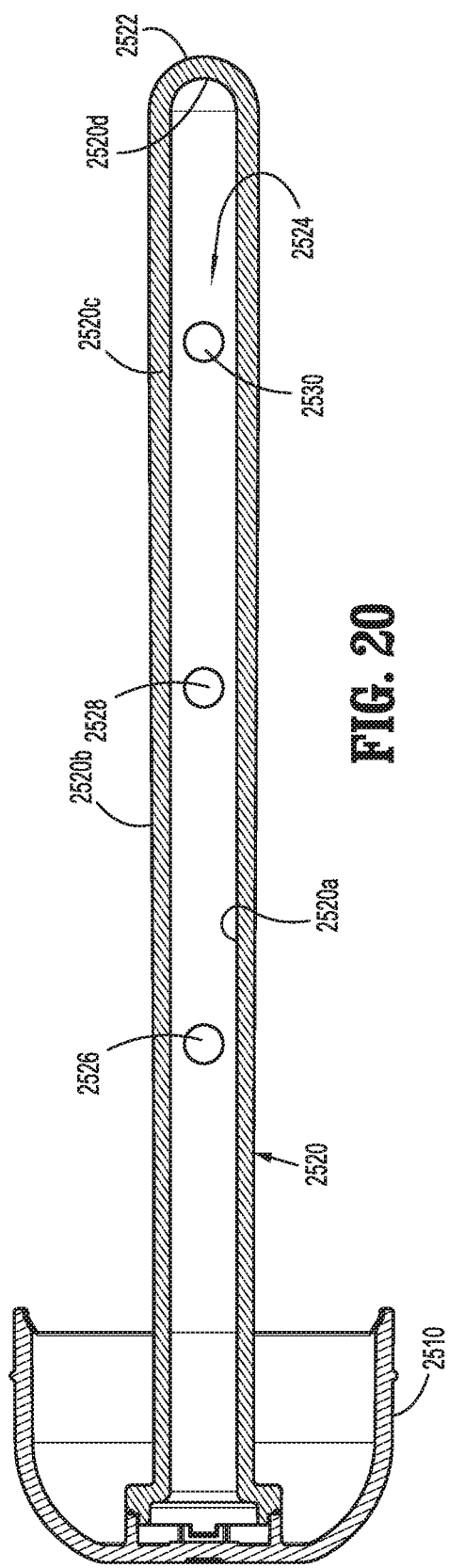

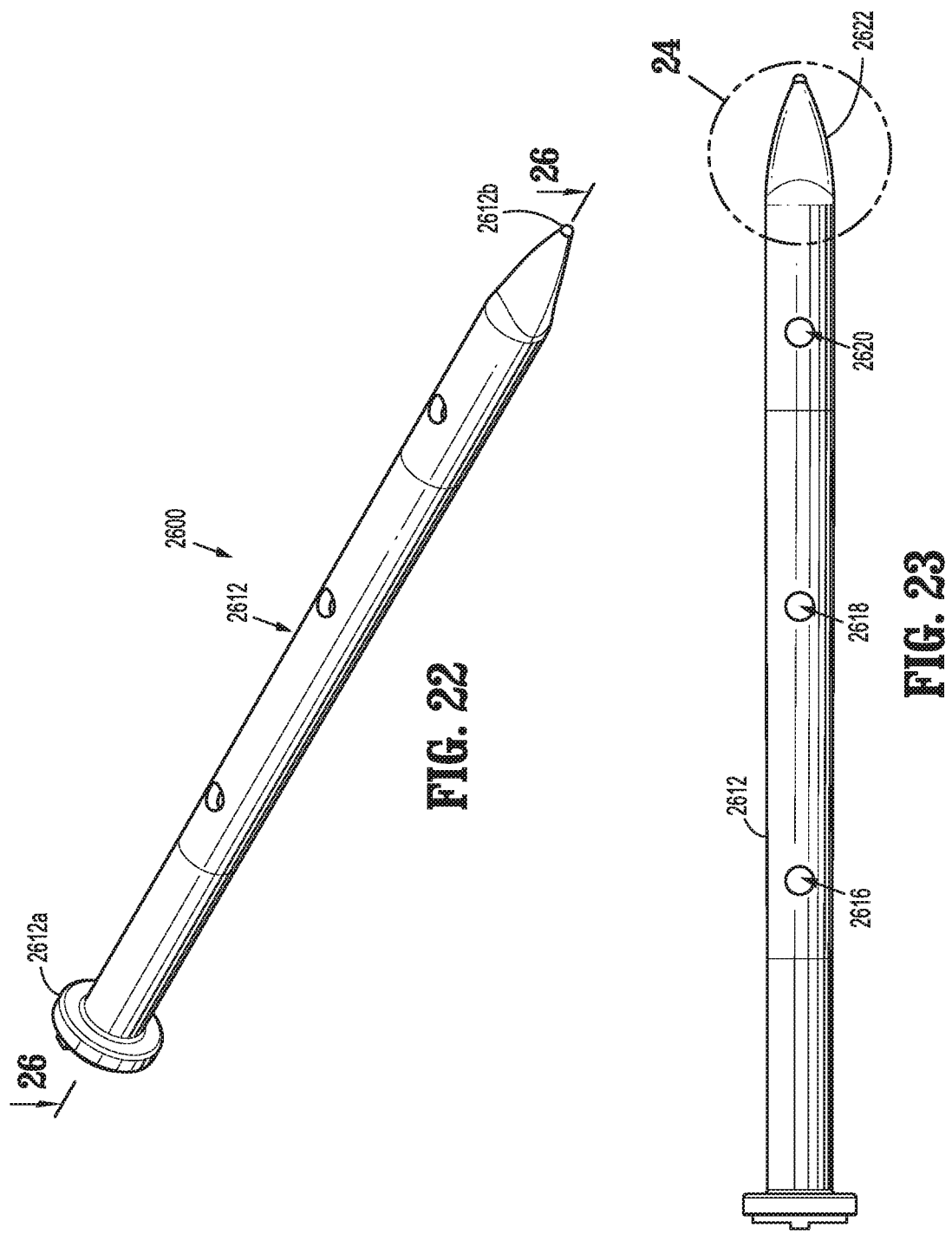

5-5

6-6

7-7

8-8

9-9

10-10

11-11

12-12

13-13

14-14

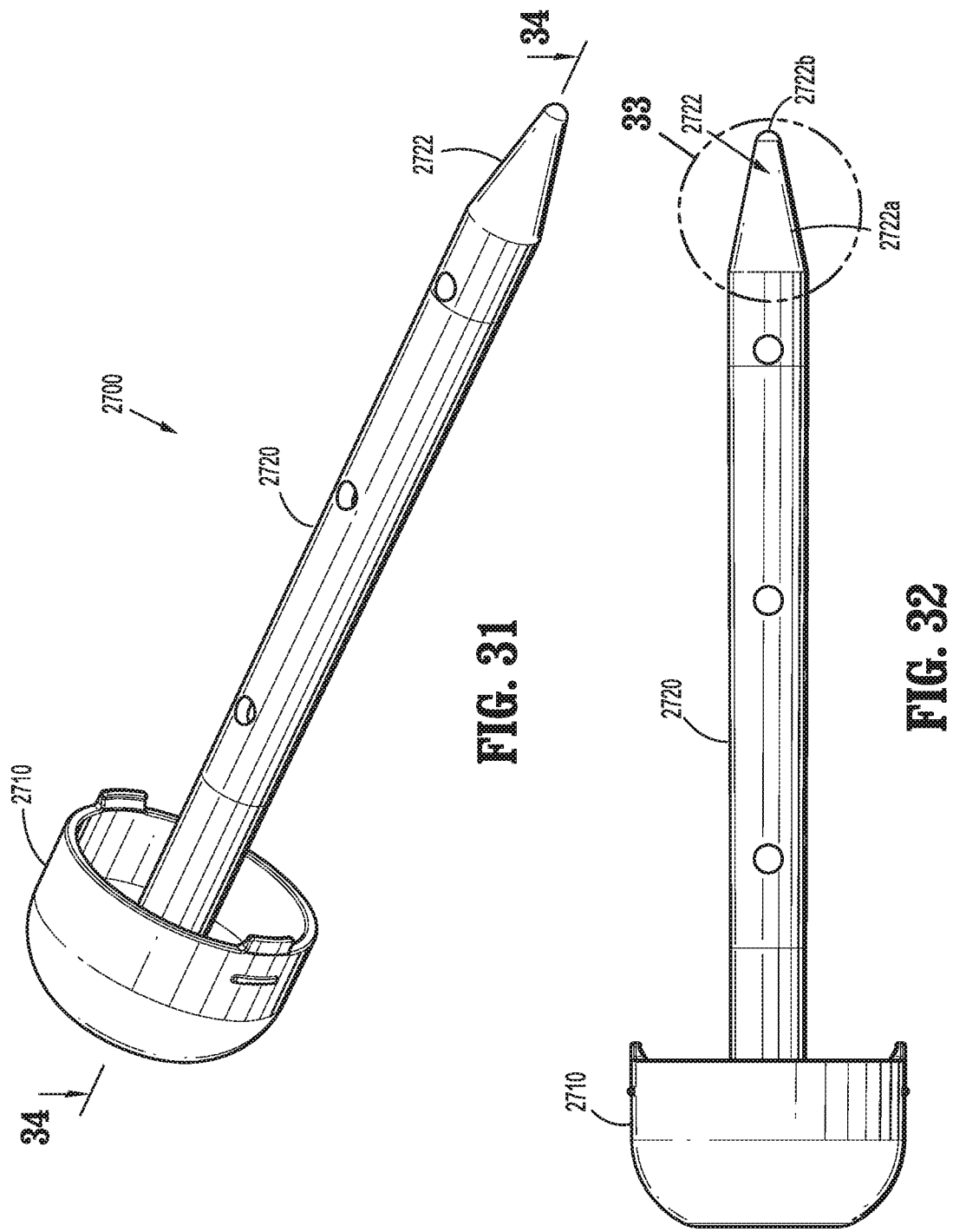

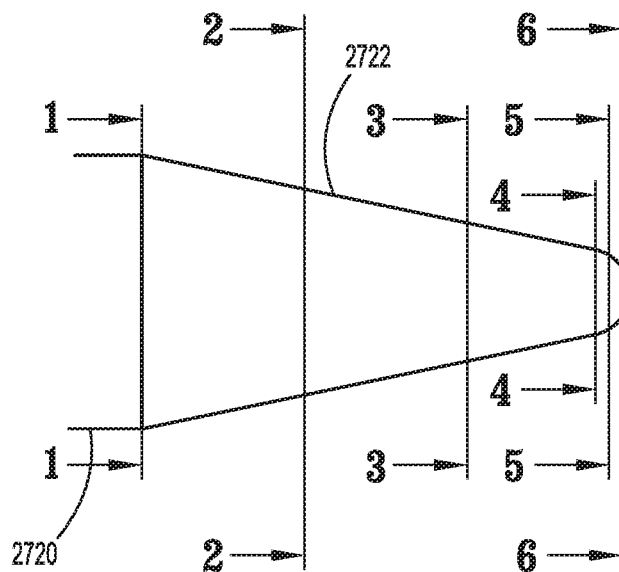
FIG. 33
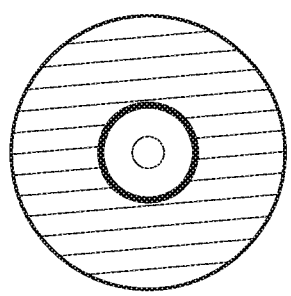 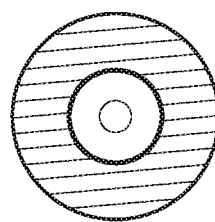 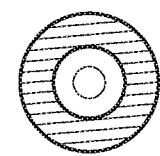
1-1　　　　　　　2-2　　　　　　　3-3
FIG. 33A　　　FIG. 33B　　　FIG. 33C
  
4-4　　　　　　　5-5　　　　　　　6-6
FIG. 33D　　　FIG. 33E　　　FIG. 33F

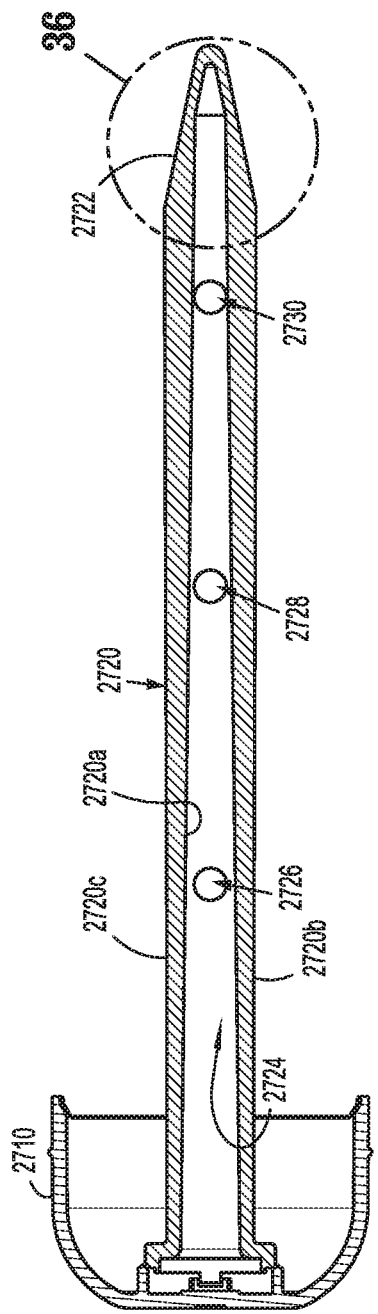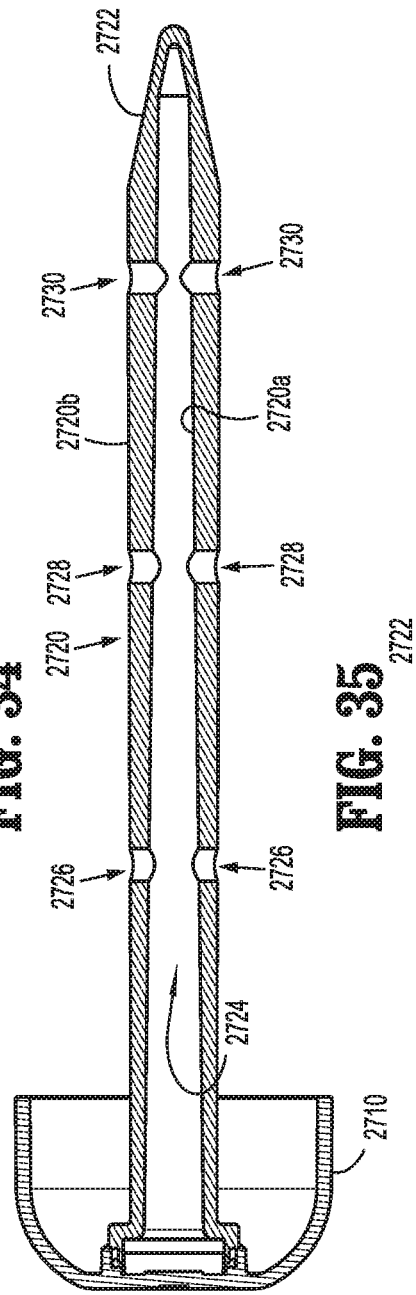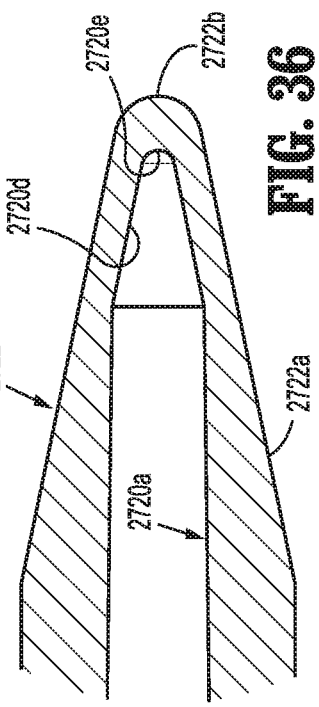

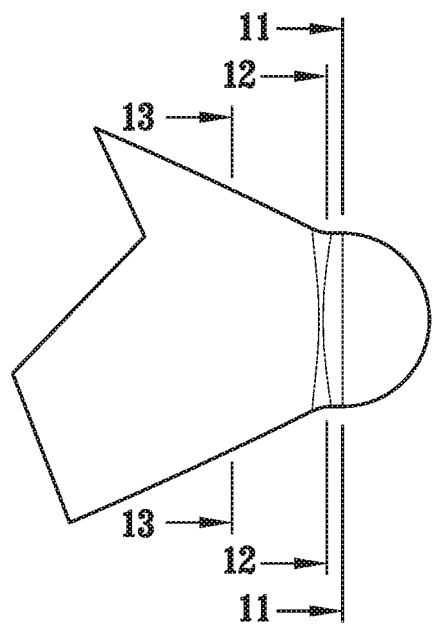
FIG. 43H
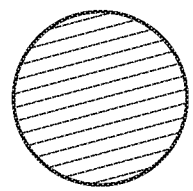
11-11
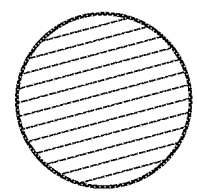
12-12
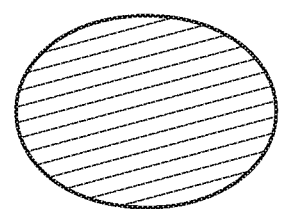
13-13

SURGICAL ACCESS DEVICE

CROSS-REFERENCE TO RELATED APPLICATIONS

This application is a continuation of U.S. application Ser. No. 15/573,661, filed Nov. 13, 2017, which is a 371 of PCT/US2016/031711, filed May 11, 2016, which claims the priority to, and the benefit of, U.S. Provisional Patent Application Ser. No. 62/161,930, filed May 15, 2015. Each of these disclosures is incorporated by reference herein in its entirety.

TECHNICAL FIELD

The present disclosure relates to a surgical access device. More particularly, the present disclosure relates to a trocar assembly.

BACKGROUND OF RELATED ART

Endoscopic and laparoscopic minimally invasive procedures have been used for introducing medical devices inside a patient and for viewing portions of the patient's anatomy. Typically, to view a desired anatomical site, a surgeon may insert a rigid or flexible endoscope inside the patient to render images of the anatomical site. In endoscopic surgical procedures, surgery is performed in any hollow organ or tissue of the body through a small incision or through narrow endoscopic tubes (cannulas) inserted through a small entrance wound in the skin. In laparoscopic procedures, surgical operations in the abdomen are performed through small incisions (usually about 0.5 to about 1.5 cm). Laparoscopic and endoscopic procedures often require the surgeon to act on organs, tissues and vessels far removed from the incision.

Typically, a trocar includes a cannula and an obturator. The cannula remains in place for use during the laparoscopic procedure, and the obturator includes a tip for penetrating the body cavity.

Accordingly, the present disclosure is directed to further improvements in trocar assemblies for use, e.g., in laparoscopic procedures.

SUMMARY

The present disclosure relates to a valve assembly for use with a surgical instrument, the valve assembly comprising: a housing; a seal assembly disposed within the housing, the seal assembly including: a septum seal including an orifice configured to sealingly engage a surgical instrument inserted therethrough, at least a portion of the septum seal defining a seal curvature; a first guard member including a plurality of curved first guard portions defining slits therebetween, each one of the plurality of curved first guard portions having a first guard curvature; a second guard member including a plurality of curved second guard portions defining slits therebetween, each one of the plurality of curved second guard portions having a second guard curvature, the first and second guard members positioned in an overlapping relationship with the plurality of first guard portions rotationally offset with respect to the second guard portions, and wherein the first guard curvature generally matches the second guard curvature and is greater than the seal curvature.

In embodiments, the first and second guard curvatures may be greater than the seal curvature so as to help prevent the first and second guard members from being inverted when an instrument is withdrawn therethrough. Also, the first and second guard curvature may be greater than the seal curvature so as to help prevent the septum seal from being inverted when an instrument is withdrawn therethrough. The valve assembly may also include an upper seal support and a lower seal support, the septum seal and the first and second guard members being retained between the upper and lower seal supports.

The slits of the first guard member may be aligned with the curved guard portions of the second guard member, and the slits of the second guard member may be aligned with the curved guard portions of the first guard member. The first and second guard members also may include respective center apertures and respective flat guard portions, one or more of the slits extending from the center aperture to the flat guard portion. Each slit may progressively increase in width as it extends radially outward from the center aperture. Each slit may be generally triangular in shape. Each slit may extend radially beyond the curved guard portions. The valve assembly may include a septum seal with bellows.

The present invention also relates, in accordance with still various embodiments, to a valve assembly for use with a surgical instrument, the valve assembly comprising: a housing; a seal assembly disposed within the housing, the seal assembly including: a septum seal including an orifice configured to sealingly engage a surgical instrument inserted therethrough; a first guard member including a plurality of first guard portions defining slits therebetween, each slit progressively increasing in width as it extends radially outward from a center aperture so as to be generally triangular in shape; a second guard member positioned in an offset relationship relative to the first guard member, the second guard member including a plurality of second guard portions defining slits therebetween, each slit progressively increasing in width as it extends radially outward from a center aperture so as to be generally triangular in shape.

In various embodiments, the septum seal may include at least a portion defining a seal curvature, the plurality of curved first and second guard portions having varying curvature. The first and second guard curvatures may be greater than the seal curvature so as to prevent one or more of the first guard portions, the second guard portions and/or the septum seal from being inverted by an instrument being withdrawn therethrough. The valve assembly may also include an upper seal support and a lower seal support, the septum seal and the first and second guard members being retained between the upper and lower seal supports. The slits of the first guard member may overlay the guard portions of the second guard member, and the slits of the second guard member overlay the curved guard portions of the first guard member. The first and second guard members may also include respective flat guard portions, one or more of the slits extending from the center aperture to the flat guard portion. Each slit may extend radially beyond the curved guard portions. The septum seal may include bellows.

The present disclosure also relates to a surgical access device comprising an obturator assembly and a cannula assembly. The obturator assembly comprises an obturator member and a tip member disposed adjacent a distal portion of the obturator member. The obturator member has an outer diameter of about 10 mm. A portion of the tip member has an outer diameter of between about 14 mm and about 15 mm. The cannula assembly comprises an elongated portion configured to allow the obturator member and the tip member to slide therethrough. An inner diameter of the elongated portion approximates the outer diameter of the tip member.

A valve assembly for use with a surgical instrument, the valve assembly comprising: a housing; a seal assembly disposed within the housing, the seal assembly including: a septum seal including an orifice configured to sealingly engage a surgical instrument inserted therethrough; a first guard member including a plurality of first guard portions defining slits therebetween, wherein, in a rest position of the first guard member, each slit progressively increases in width as it extends radially outward from a center aperture such that the slits are generally triangular in shape; a second guard member positioned in an offset relationship position relative to the first guard member, the second guard member including a plurality of second guard portions defining slits therebetween, wherein, in a rest position of the second guard member, each slit progressively increases in width as it extends radially outward from a center aperture such that the slits are generally triangular in shape.

In embodiments, the septum seal includes at least a portion defining a seal curvature, the plurality of curved first and second guard portions having varying curvature. The first and second guard curvatures may be greater than the seal curvature so as to prevent one or more of the first guard portions, the second guard portions and the septum seal from being inverted by an instrument being withdrawn therethrough. The valve assembly may also include an upper seal support and a lower seal support, the septum seal and the first and second guard members being retained between the upper and lower seal supports. The slits of the first guard member may align with the guard portions of the second guard member, and the slits of the second guard member align with the curved guard portions of the first guard member. The first and second guard members may also include respective flat guard portions, one or more of the slits extending from the center aperture to the flat guard portion. Each slit may extend radially beyond the curved guard portions.

In embodiments, the septum seal may include bellows. The first and second guard members may both be located proximally of the septum seal. The first and second guard members may both be located distally of the septum seal. The valve assembly may also include a third guard member and a fourth guard member, the first and second guard members being located proximally of the septum seal and the third and fourth guard members located distally of the septum seal.

BRIEF DESCRIPTION OF THE DRAWINGS

The above and other aspects, features, and advantages of the present disclosure will become more apparent in light of the following detailed description when taken in conjunction with the accompanying drawings in which:

FIG. 5B is a cross-sectional view of the valve assembly of FIG. 5A as assembled;

FIG. 11 is a cut-away perspective view taken along line 11-11 in FIG. 9;

FIG. 12 is a cut-away perspective view taken along line 12-12 in FIG. 9;

FIG. 19 is a cross-sectional view of the obturator of FIG. 16, taken along section line 19-19;

FIG. 20 is a cross-sectional view of the obturator of FIG. 19 rotationally offset by 90 degrees, taken along section line 20-20;

FIG. 22 is a perspective view of a second embodiment of an obturator for separating tissue planes in an endoscopic surgical procedure;

FIG. 23 is a side view of the obturator of FIG. 22;

FIG. 31 is a perspective view of a third embodiment of an obturator for separating tissue planes in an endoscopic surgical procedure;

FIG. 32 is a side view of the obturator of FIG. 31;

FIG. 33 is an enlarged top view of the distal portion of the elongate shaft of the obturator of FIG. 31;

FIGS. 33A-33F show cross-sections of the distal portion taken along lines 1-1, 2-2, 3-3, 4-4, 5-5, and 6-6;

FIG. 34 is a cross-sectional view of the obturator of FIG. 31;

FIG. 35 is a cross-sectional view of the obturator of FIG. 34 rotationally offset by 90 degrees;

FIG. 36 is an enlarged cross-sectional view of the distal portion of the elongate shaft of the obturator of FIG. 31 of the area of detail;

FIG. 43F-43H are top views of the distalmost nub of the distal end of the surgical access system of FIG. 38, including various cross-sectional views of the distal tip at various longitudinal positions;

DETAILED DESCRIPTION

Figure 1:
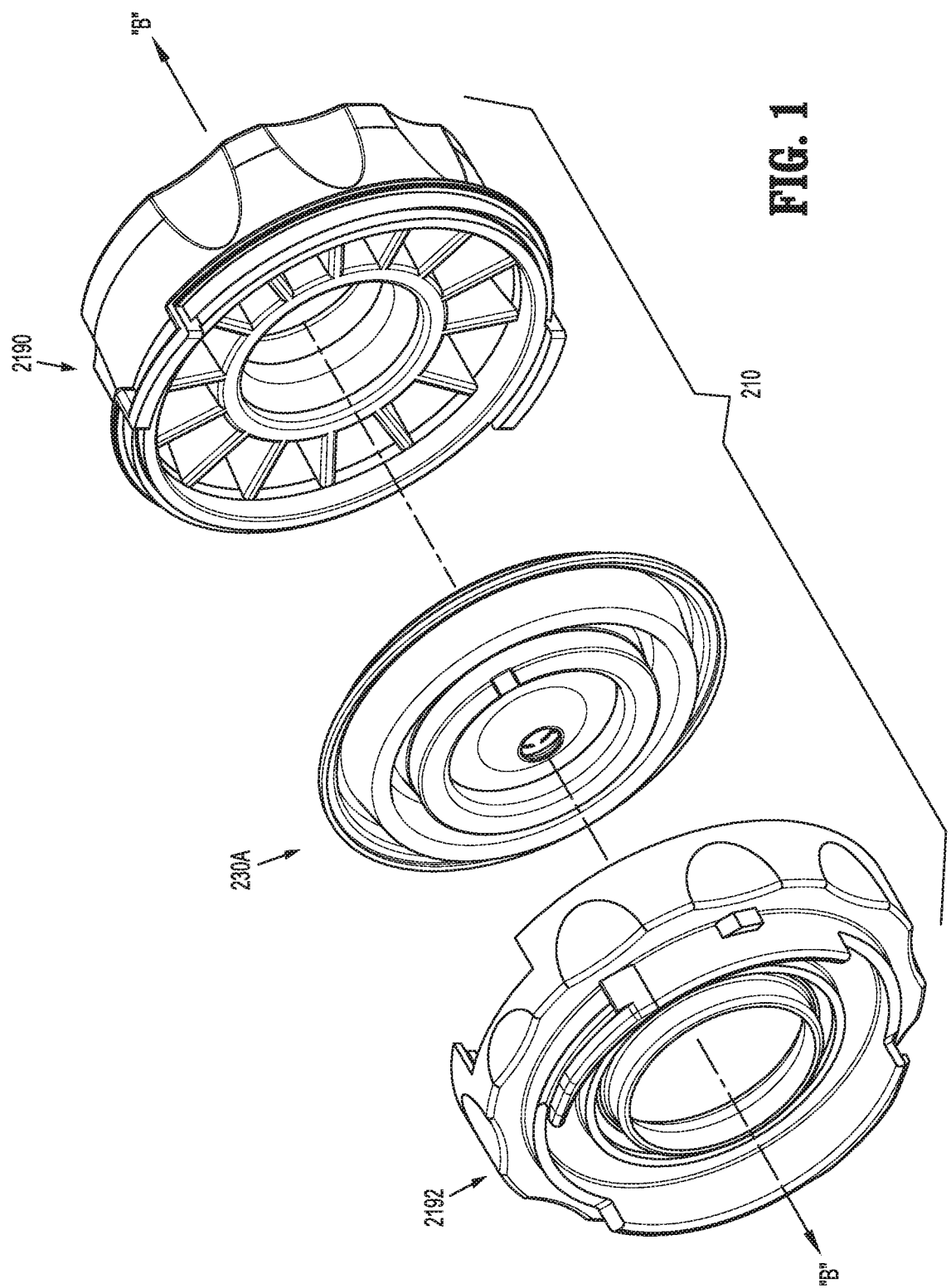
FIG. 1 is a perspective, assembly view of a valve assembly and a portion of a housing.

Particular embodiments of the present disclosure are described hereinbelow with reference to the accompanying drawings; however, it is to be understood that the disclosed embodiments are merely exemplary of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure. Like reference numerals refer to similar or identical elements throughout the description of the figures.

As used herein, the term "distal" refers to that portion of the instrument, or component thereof which is farther from the user while the term "proximal" refers to that portion of the instrument or component thereof which is closer to the user.

In various embodiments, the present invention relates to aspects of a trocar assembly. The trocar assembly may be employed during, e.g., laparoscopic surgery and may, in various embodiments, provide for the sealed access of laparoscopic surgical instruments into an insufflated body cavity, such as the abdominal cavity. Generally, and as will be described in additional detail below, the trocar assemblies of the present invention include a trocar cannula (having a valve housing mounted on a cannula tube) and a trocar obturator insertable therethrough. The trocar cannula and obturator are separate components but are capable of being selectively connected together. For example, the obturator may be inserted into and through the trocar cannula until the handle of the obturator engages, e.g., selectively locks into, the proximal valve housing of the trocar cannula. In this initial position, the trocar assembly is employed to tunnel through an anatomical structure, e.g., the abdominal wall, either by making a new passage through the structure or by passing through an existing opening through the structure. Once the trocar assembly has tunneled through the anatomical structure, the trocar obturator is removed, leaving the trocar cannula in place in the structure, e.g., in the incision created by the trocar assembly. The proximal valve housing of the trocar cannula may include valves that prevent the escape of insufflation gases from the body cavity, while also allowing surgical instruments to be inserted into the cavity.

With respect to the trocar obturators, in various embodiments, a bladeless optical obturator—an example of which is set forth in additional detail below—may be provided that permits separation of tissue planes in a surgical procedure and visualization of body tissue fibers as they are being separated, thereby permitting a controlled traversal across a body wall. In other embodiments, the obturator may be bladeless without being optical, e.g., without providing contemporaneous visualization thereof through the distal tip of an obturator. The bladeless obturator may be provided for the blunt dissection of the abdominal lining during a surgical procedure. Various examples of obturator components are disclosed and illustrated herein, e.g., bladed, bladeless, blunt, optical, non-optical, etc. as will be described in additional detail below. However, it should be recognized that various other types of obturators may be employed, e.g., obturators having tip geometries other than those shown.

The proximal valve housing of the trocar cannula may include various arrangements and/or components. In various embodiments, the proximal valve housing includes an instrument valve assembly (having an instrument valve component) that is selectively attachable to, and detachable from, a distal housing component (which may or may not be permanently attached to a cannula tube and which may or may not include additional valves, e.g., a zero seal valve such as a duckbill valve. Example embodiments of such arrangements are set forth in greater detail below.

With reference to FIGS. 1-15, and with particular reference to FIG. 1, instrument valve assembly 210 includes a first housing portion 2190, a second housing portion 2192 and instrument valve component or valve assembly 230A. Instrument valve component 230A is positioned between and maintained within first housing portion 2190 and second housing portion 2192. First housing portion 2190 and second housing portion 2192 of instrument valve assembly 210 may be welded together.

Figure 2:
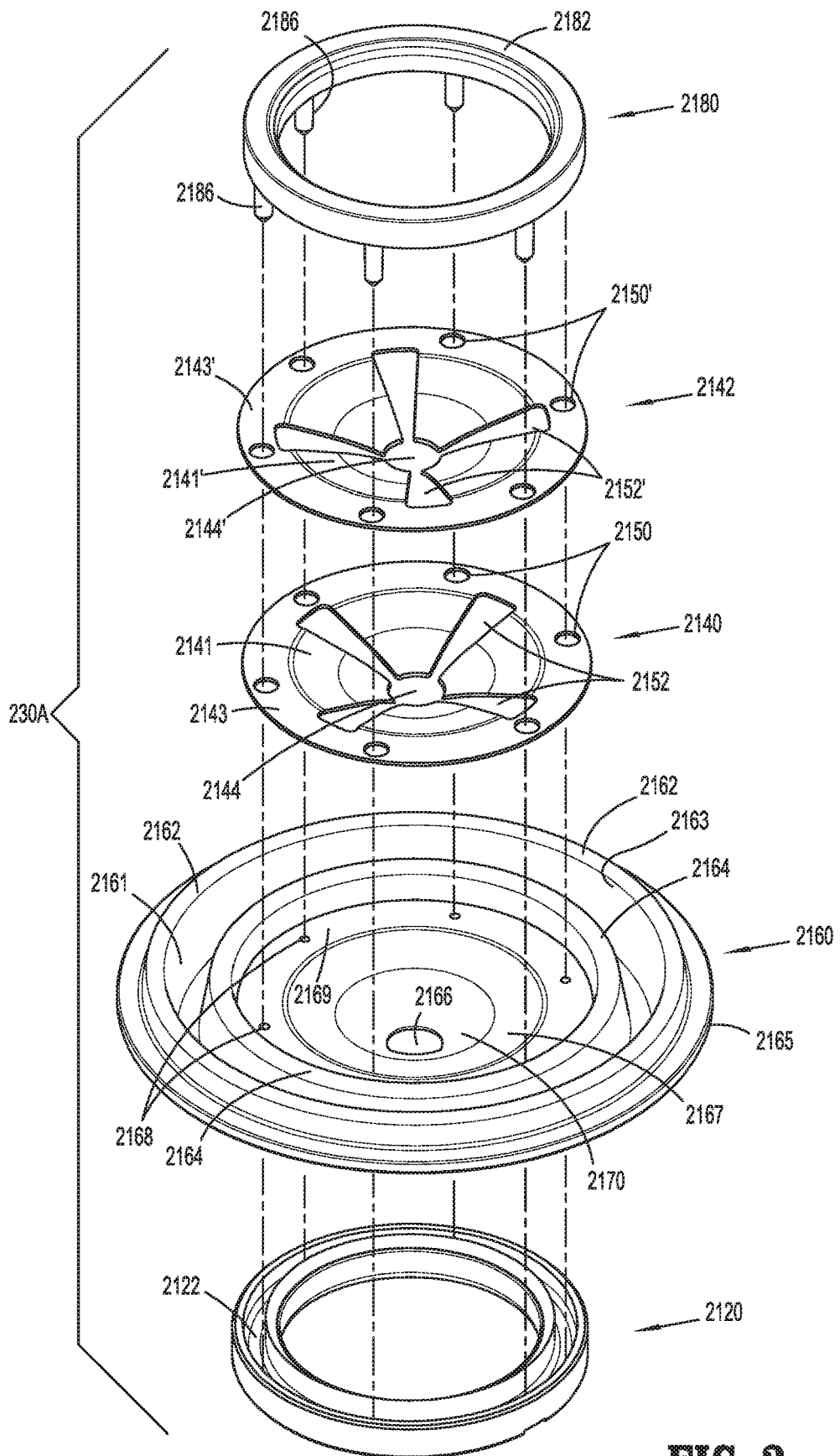
FIG. 2 is a perspective view, with parts separated, of the valve assembly.

With reference to FIG. 2, instrument valve component 230A includes an elastomeric septum seal 2160, a lower seal retainer 2120, and an upper seal retainer 2180. Lower seal retainer 2120 and upper seal retainer 2180 may be referred to as a lower seal support and an upper seal support, respectively. Instrument valve component 230A further includes first and second guard members 2140, 2142. In alternate embodiments, fewer or more guard members (see FIGS. 5A-5D) than the two guard members shown herein may be employed.

With reference to FIG. 2, septum seal 2160 is configured to provide a seal around an outer surface of an instrument passing therethrough. Septum seal 2160 includes a bellowed outer seal portion 2163, an intermediate flat guard portion 2169, and a curved inner seal portion 2167 (or first sloped portion). The bellowed outer seal portion 2163 includes an inner bellows 2164, an outer bellows 2162 and a radially outermost lip 2165. Flat guard portion 2169 includes a plurality of apertures 2168 annularly disposed therethrough. Inner seal portion 2167 has an orifice 2166 at its radial center. It should be noted that, while the bellowed outer seal portion 2163 is shown and described herein as having an inner and outer bellows, in alternate embodiments, fewer or more bellows may be employed.

Curved inner seal portion 2167 (or first sloped portion) is disposed between flat guard portion 2169 and second sloped portion 2170 (FIG. 2). Curved inner seal portion 2167 may be sloped at a first angle, whereas second sloped portion 2170 may be sloped at a second angle, where the first and second angles are different. In particular, the angle of second sloped portion 2170 may be greater than the angle of curved inner seal portion 2167. Second sloped portion 2170 is configured to accommodate orifice 2166 of septum seal 2160. The varying angles of curved portions 2167, 2170 of septum seal 2160 may facilitate guiding instrument 211 (FIG. 15) toward orifice 2166. In addition, varying the angles of curved portions 2167, 2170 of septum seal 2160 may help prevent the septum seal 2160 from inverting when an instrument is withdrawn.

Upper seal retainer 2180 includes a ring 2182 and a plurality of fingers or pins 2186 extending downwardly from ring 2182. Lower seal retainer 2120 is a ring that includes an annular channel 2122. It should be recognized that, although the plurality of fingers or pins 2186 is shown as extending downwardly from upper seal retainer 2180 for engagement with the lower seal retainer 2120, in other embodiments, the plurality of fingers or pins 2186 may instead extend upwardly from lower seal retainer 2120 for engagement with the upper seal retainer 2180, or the pins and fingers may be located on both the upper and lower seal retainers 2120, 2180 and extend both upwardly and downwardly. In addition, it should also be recognized that, while the lower seal retainer 2120 is shown and described herein as including an annular channel 2122, the lower seal retainer 2120 may instead include one or more discrete openings for receiving the corresponding fingers or pins, which may improve the engagement of the pins/fingers with the lower seal ring and increase the retention therebetween once connected to each other. An advantage of employing a channel, however, is that circumferential alignment of the upper and lower rings prior to connecting them may be avoided.

First guard member 2140 includes a plurality of curved guard portions 2141 and a flat guard portion 2143. Flat guard portion 2143 includes a plurality of apertures 2150 annularly disposed therethrough. The plurality of curved guard portions 2141 collectively define an orifice 2144 at their radial center. First guard member 2140 further defines a plurality of slits 2152 between the plurality of curved guard portions 2141 and extending from orifice 2144 toward flat guard portion 2143. Slits 2152 include four slits that define a substantially "cross" configuration.

Second guard member 2142 includes a plurality of curved guard portions 2141' and a flat guard portion 2143'. Flat guard portion 2143' includes a plurality of apertures 2150' annularly disposed therethrough. The plurality of curved guard portions 2141' collectively define an orifice 2144' at their radial center. Second guard member 2142 further defines a plurality of slits 2152' between the plurality of curved guard portions 2141' and extending from orifice 2144' toward flat guard portion 2143'. Slits 2152' include four slits that define a substantially "cross" configuration.

While first and second guard members 2140, 2142 are shown and described herein as each having four slits 2152, 2152', respectively, it should be recognized that a greater number or a lesser number of slits for each guard member 2140, 2142 may be employed. Likewise, while first and second guard members 2140, 2142 are shown and described herein as each having four guard portions 2141, 2141', respectively, it should be recognized that a greater number or a lesser number of guard portions for each guard member 2140, 2142 may also be employed. For example, slits and/or guard portions numbering between 2 and 10 for each guard member 2140, 2142 are contemplated.

Additionally, while each slit 2152, 2152' and each guard portion 2141, 2141' is shown to be substantially triangular in shape, it should be recognized that other geometrical shapes for each of slits 2152, 2152' and guard portions 2141, 2141' of the first and second guard members 2140, 2142, respectively, may be employed. Still further, while the guard portions 2141, 2141' are shown and described herein as being curved, such guard portions could instead be straight or may each have multiple curved portions. In an embodiment, each of the guard portions 2141, 2141' may have a curvature that match the curvature of the curved inner seal portion 2167 of the septum seal 2160. Additionally or alternatively, each of the guard portions 2141, 2141' may have a curvature that exceeds, e.g., that is more curved than, the curvature of the curved inner seal portion 2167 of the septum seal 2160—such an arrangement may help prevent the curved inner seal portion 2167 of the septum seal 2160 and the guard portions 2141, 2141' from being inverted, e.g., bent proximally, when an instrument is withdrawn therethrough.

Figure 3:
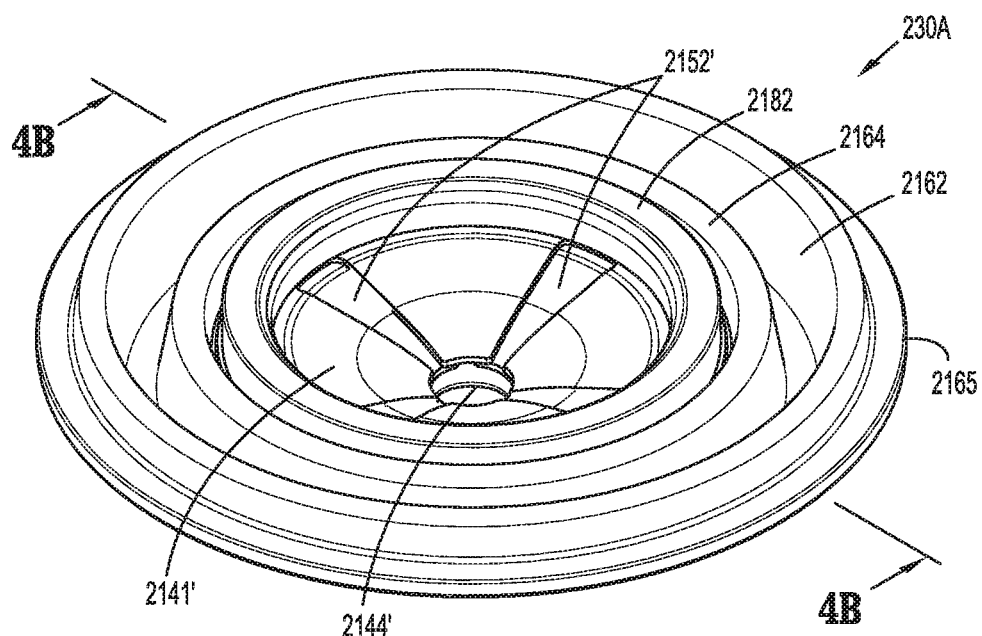
FIG. 3 is a perspective view of the valve assembly.
Figure 4A:
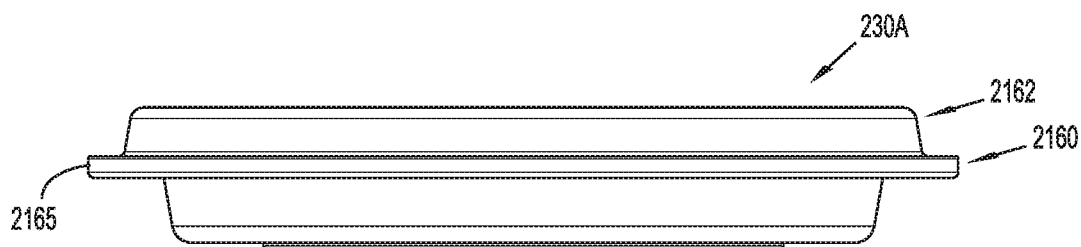
FIG. 4A is a side view of the valve assembly.
Figure 4B:
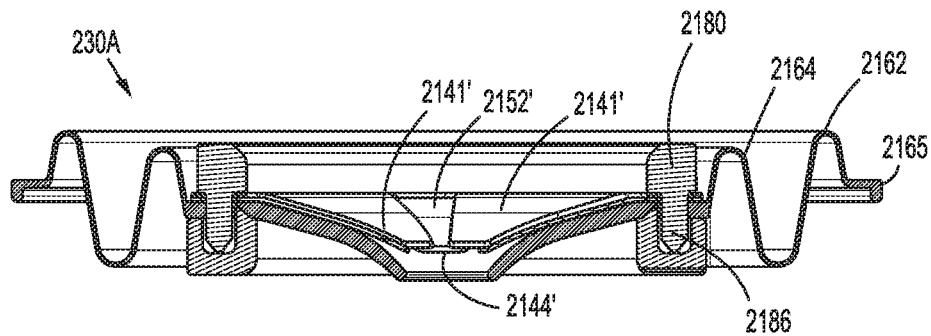
FIG. 4B is a cross-sectional view of the valve assembly taken along line 4B-4B in FIG. 3.

FIG. 3 is an assembled view of instrument valve assembly 210, while FIGS. 4A and 4B are a side view and a side cross-sectional view, respectively, of instrument valve component 230A. When instrument valve component 230A is assembled, pins 2186 of upper seal retainer 2180, apertures 2150, 2150' of first and second guard members 2140, 2142, and apertures 2168 of septum seal 2160 are longitudinally aligned, such that each one of pins 2186 extend through respective ones of apertures 2150, 2150' of first and second guard members 2140, 2142 and through respective ones of apertures 2168 of septum seal 2160. The distalmost ends of pins 2186 engage annular channel 2122 of lower seal retainer 2120 and are retained therein by any suitable technique, such as by snap-fit, friction-fit, welding, etc., such that septum seal 2160 and first and second guard members 2140, 2142 are secured between upper seal retainer 2180 and lower seal retainer 2120.

As shown in FIGS. 3-4B, when instrument valve component 230A is assembled, first and second guard members 2140, 2142 are rotationally offset with respect to each other by 90 degrees (relative to the longitudinal axis), such that slits 2152 of first guard member 2140 and slits 2152' of second guard member 2142 are also rotationally offset from each other by 90 degrees (relative to the longitudinal axis). The rotational offset of first and second guard members 2140, 2142 with respect to each other provides for the plurality of curved guard portions 2141 of first guard member 2140 to span the width of slits 2152' of second guard member 2142, and for the plurality of curved guard portions 2141' of second guard member 2142 to span the width of slits 2152 of first guard member 2140.

The rotational offset of first and second guard members 2140, 2142 with respect to each other facilitates the protection of septum seal 2160 when instrument valve component 230A is disposed within the housing of a cannula assembly 200 (FIG. 6) and an instrument is inserted through orifices 2144, 2144'. It should be recognized that the first and second guard members 2140, 2142 may instead be aligned with each other, depending on the shape and number of the guard portions. Additionally, it should be recognized that the first and second guard members 2140, 2142 may be misaligned by more or less than 90 degrees with respect to each other, depending on the shape and number of the guard portions.

In the embodiment shown in, e.g., FIG. 4B, the height of outer bellows 2162 is greater than the height of inner bellows 2164. Inner and outer bellows 2164, 2162 extend generally perpendicular to flat guard portion 2169. Inner and outer bellows 2164, 2162 extend generally radially on septum seal 2160. In other embodiments, the height of inner and outer bellows 2164, 2162 may be substantially equal, or the height of inner bellows 2164 may be greater than the height of outer bellows 2162. Additionally, the width of inner bellows 2164 may be substantially equal to the width of outer bellows 2162. The width of inner bellows 2164 may be greater than or less than the width of outer bellows 2162. For example, outer bellows 2162 may be twice the width of inner bellows 2164, or vice versa.

In the embodiment shown, each one of the slits 2152 of the first guard member 2140 has an equal width and length with respect to the other slits 2152. For example, as shown, the width of each one of the slits 2152 progressively increases as slits 2152 extend from the orifice 2144 to the flat guard portion 2143 so as to define a substantially triangular configuration. Therefore, the narrowest part of slits 2152 is near orifice 2144 and the width of each slit 2152 increases from a distal end 2147 to a proximal end 2149 of each slit 2152. Moreover, in the embodiment shown, the width of curved guard portions 2141 is greater at a given radial location than the width of slits 2152. For example, the width of a curved guard portion 2141, at a given radial location, may be more than twice the width of a slit 2152. The width of slits 2152 may be selected such that the guard portions 2141 experience adequate flexibility when surgical instrument 211 (FIG. 15) is inserted through orifice 2144 while still providing adequate protection to the septum seal 2160 upon insertion and withdrawal of an instrument.

In various embodiments, the slits 2152 may extend beyond curved guard portion 2141 and into flat guard portion 2143. Slits 2152 may or may not extend to the outer radial edge of flat guard portion 2143, although having slits 2152 not extend to the outer radial edge of flat guard portion 2143 may provide the advantage of the first guard member 2140 being a single component that is more easily handled during manufacture. Slits 2152 may extend less than half the length of flat guard portion 2143. This extension of slits 2152 beyond curved guard portion 2141 may provide for additional flexibility of the curved guard portions 2141, as well as first guard member 2140, when a surgical instrument 211 is inserted through orifice 2144.

Advantageously, the slits 2152' and curved guard portions 2141' of second guard member 2142 may exhibit the same geometries as described above with regard to slits 2152 and curved guard portions 2141, respectively, of first guard member 2140. Curved guard portion 2141 may have a first curvature or angle, and curved guard portion 2141' may have a second curvature or angle, where the first and second angles/curvatures are equal to each other. When second guard member 2141 is positioned adjacent to or in abutting relationship with first guard member 2140, the matching angles/curvatures of curved guard portions 2141, 2141' may allow for a relatively smooth surface with minimal voids therebetween, reducing the likelihood of an instrument or feature of an instrument sliding between or getting trapped between the respective guard members. It should also be recognized that, if the slits 2152' and curved guard portions 2141' of second guard member 2142 have the same geometries as slits 2152 and curved guard portions 2141 of first guard member 2140, the first and second guard members 2140, 2142 may also have the same overall geometries, enabling them to be formed on the same tools/molds so as to achieve manufacturing and assembly efficiencies.

In the embodiment shown, the diameter of first guard member 2140 is substantially equal to the diameter of second guard member 2142. The diameter of septum seal 2160 may be greater than the diameter of first and second guard members 2140, 2142. First and second guard members 2140, 2142 are adapted and dimensioned to be accommodated within the inner boundaries of inner bellows 2164 of septum seal 2160 such that the outer peripheral edge of first and second guard members 2140, 2142 contacts the inner bellows 2164. Manipulation of surgical instrument 211, while in orifice 2166 of septum seal 2160, causes the inner and outer bellows 2164, 2162 to move. The flexibility provided by bellows 2164, 2162 helps to minimize the likelihood that an instrument positioned within the aperture 2166 of the septum seal 2160 will cause the orifice to cat-eye and thereby leak insufflation gas. In addition, the bellows 2164, 2162 function to move the aperture 2166 of the septum seal 2160 back to the central longitudinal axis B of the device when no instrument is positioned therein, which also increases the likelihood that a subsequently inserted instrument will travel through the aperture 2166, and minimizes the likelihood that such a subsequently inserted instrument will contact the radially outer portions of the septum seal and thereby tear it.

Once instrument valve component 230A has been assembled as shown in FIGS. 3-4B, it is incorporated into instrument valve assembly 210 as shown in FIG. 1. Specifically, instrument valve component 230A is maintained in position within instrument valve assembly 210 by positioning radially outermost lip 2165 of valve component 230A between first and second housing portions 2190, 2192 of proximal housing component 210a (FIGS. 9-12) and then connecting, e.g., by snap-fit, welding, etc., first and second housing portions 2190, 2192 together.

Assembled instrument valve assembly 210 is selectively attachable to, and detachable from, various types of distal cannula assemblies (shown and described in further detail below) in order to collectively provide various types of cannula assemblies.

Figure 5A:
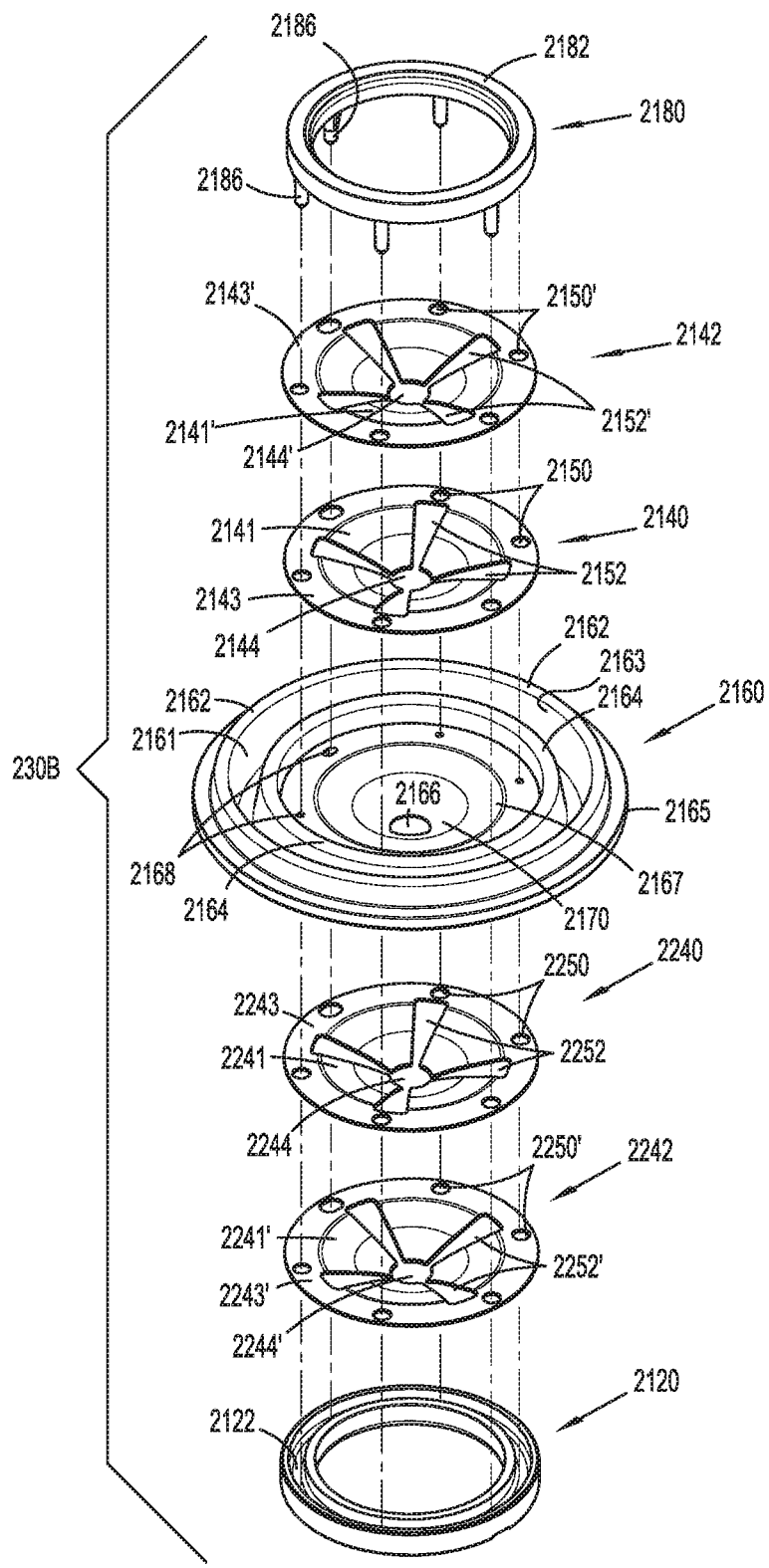
FIG. 5A is a perspective view, with parts separated, of another embodiment of a valve assembly.

FIGS. 5A-5D illustrate another embodiment of an instrument valve component or valve assembly 230B. With reference to FIG. 5A, instrument valve component 230B includes an elastomeric septum seal 2160, a lower seal retainer 2120, and an upper seal retainer 2180. Lower seal retainer 2120 and upper seal retainer 2180 may be referred to as a lower seal support and an upper seal support, respectively. Instrument valve component 230B further includes first and second guard members 2140, 2142. All these elements have been described above with reference to FIGS. 2-4B and their description will be omitted for sake of clarity. In contrast to FIGS. 2-4B, FIGS. 5A-5D illustrate a third guard member 2240 and a fourth guard member 2242 directly beneath or at a distal end of the septum seal 2160.

Third guard member 2240 includes a plurality of curved guard portions 2241 and a flat guard portion 2243. Flat guard portion 2243 includes a plurality of apertures 2250 annularly disposed therethrough. The plurality of curved guard portions 2241 collectively define an orifice 2244 at their radial center. Third guard member 2240 further defines a plurality of slits 2252 between the plurality of curved guard portions 2241 and extending from orifice 2244 toward flat guard portion 2243. Slits 2252 include four slits that define a substantially "cross" configuration.

Fourth guard member 2242 includes a plurality of curved guard portions 2241' and a flat guard portion 2243'. Flat guard portion 2243' includes a plurality of apertures 2250' annularly disposed therethrough. The plurality of curved guard portions 2241' collectively define an orifice 2244' at their radial center. Fourth guard member 2242 further defines a plurality of slits 2252' between the plurality of curved guard portions 2241' and extending from orifice 2244' toward flat guard portion 2243'. Slits 2252' include four slits that define a substantially "cross" configuration.

While third and fourth guard members 2240, 2242 are shown and described herein as each having four slits 2252, 2252', respectively, it should be recognized that a greater number or a lesser number of slits for each guard member 2240, 2242 may be employed. Likewise, while third and fourth guard members 2240, 2242 are shown and described herein as each having four guard portions 2241, 2241', respectively, it should be recognized that a greater number or a lesser number of guard portions for each guard member 2240, 2242 may also be employed. For example, slits and/or guard portions numbering between two and ten for each guard member 2240, 2242 are contemplated.

Additionally, while each slit 2252, 2252' and each guard portion 2241, 2241' is shown to be substantially triangular in shape, it should be recognized that other geometrical shapes for each of slits 2252, 2252' and guard portions 2241, 2241' of the third and fourth guard members 2240, 2242, respectively, may be employed. Still further, while the guard portions 2241, 2241' are shown and described herein as being curved, such guard portions could instead be straight or may each have multiple curved portions. In an embodiment, each of the guard portions 2241, 2241' may have a curvature that is similar to or matches the curvature of the curved inner seal portion 2167 of the septum seal 2160. Additionally or alternatively, each of the guard portions 2241, 2241' may have a curvature that is less than or exceeds the curvature of the curved inner seal portion 2167 of the septum seal 2160.

Figure 5C:
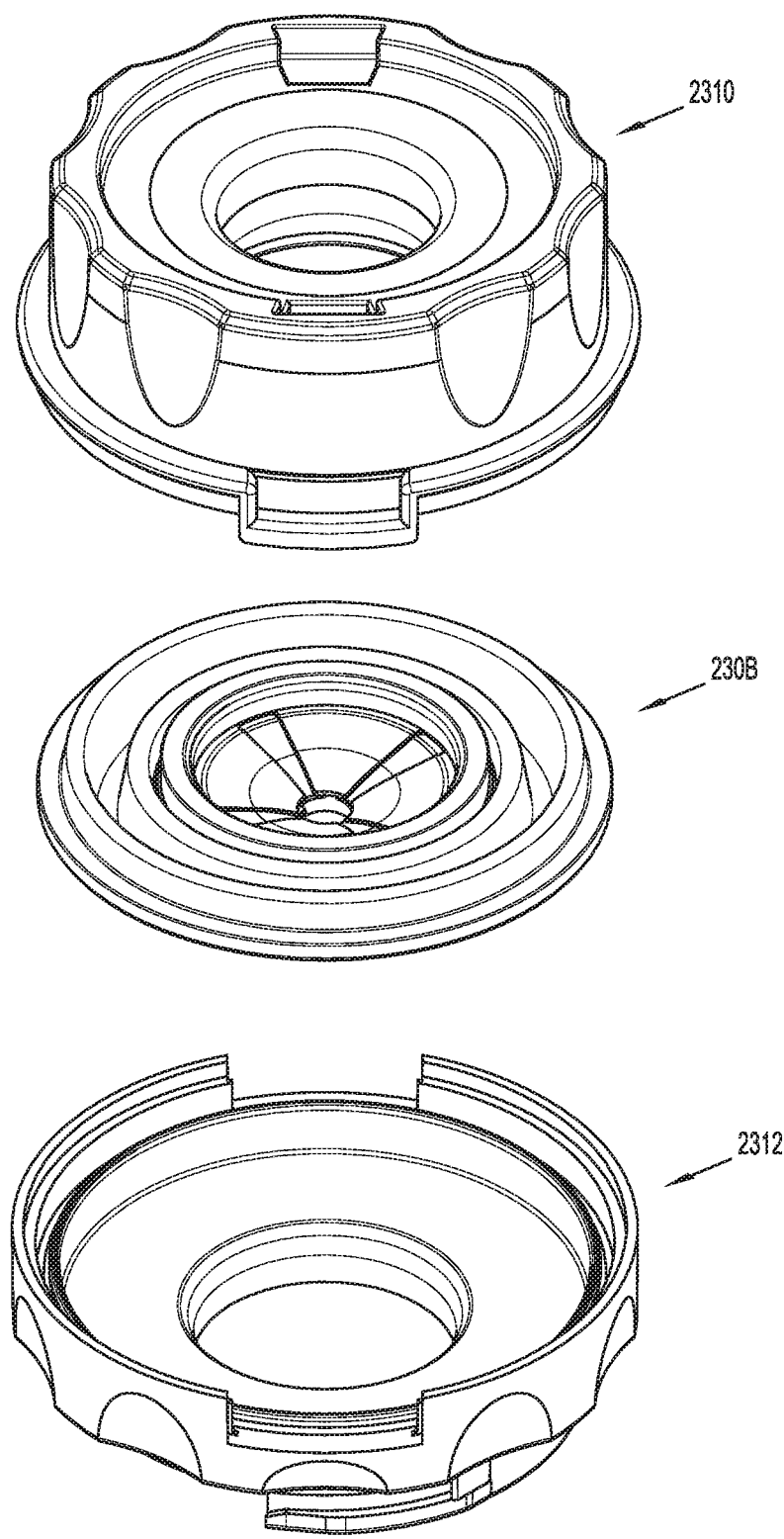
FIG. 5C is a perspective, assembly view of the valve assembly of FIG. 5A and a portion of the housing.
Figure 5D:
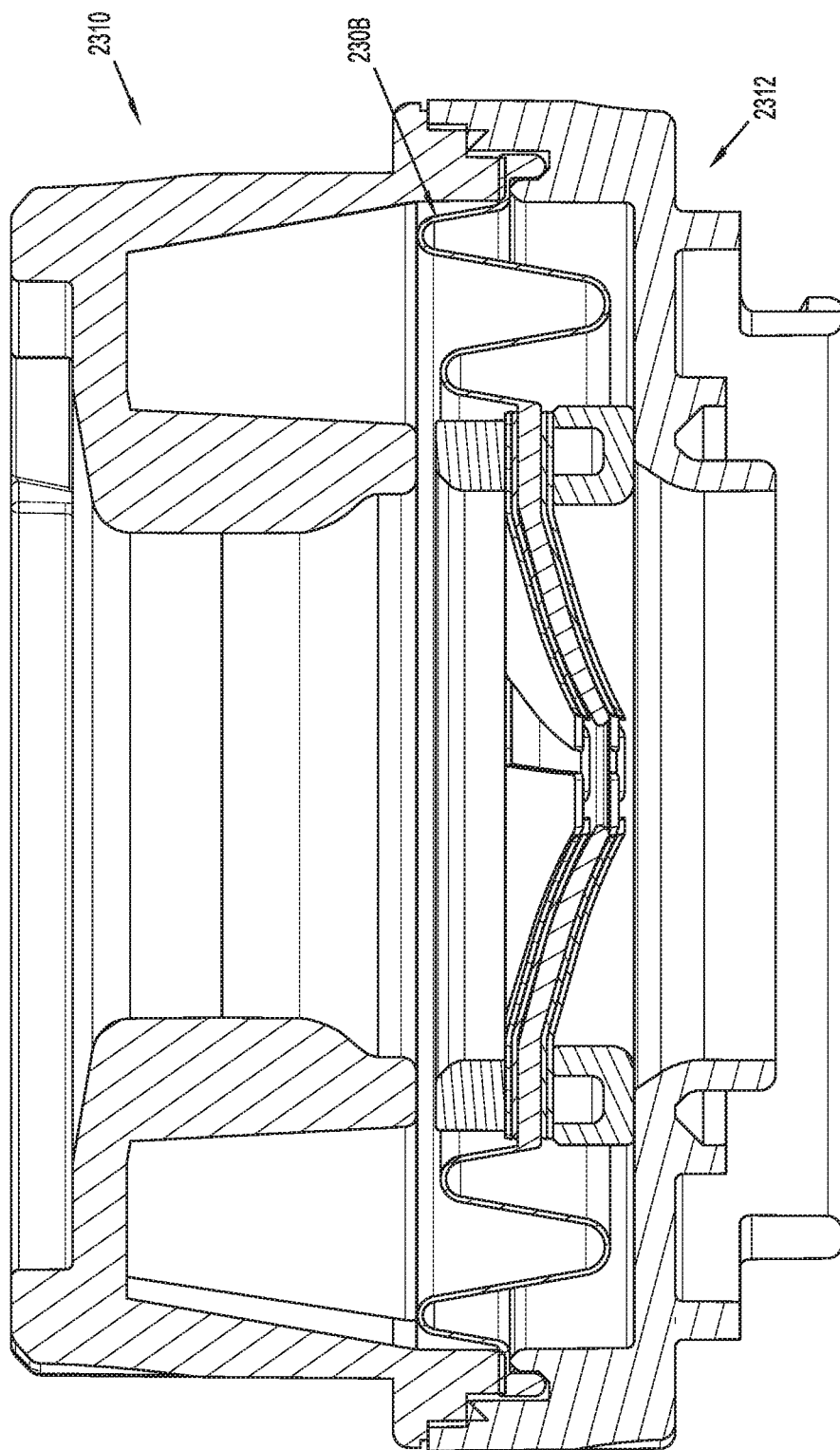
FIG. 5D is a cross-sectional view of the valve assembly of FIG. 5A assembled within the housing.

As shown in FIGS. 5B-5D, when instrument valve component 230B is assembled, first and second guard members 2140, 2142 are rotationally offset with respect to each other by 45 degrees (relative to the longitudinal axis), such that slits 2152 of first guard member 2140 and slits 2152' of second guard member 2142 are also rotationally offset from each other by 45 degrees (relative to the longitudinal axis). The rotational offset of first and second guard members 2140, 2142 with respect to each other provides for the plurality of curved guard portions 2141 of first guard member 2140 to span the width of slits 2152' of second guard member 2142, and for the plurality of curved guard portions 2141' of second guard member 2142 to span the width of slits 2152 of first guard member 2140.

Additionally, third and fourth guard members 2240, 2242 are rotationally offset with respect to each other by 45 degrees (relative to the longitudinal axis), such that slits 2252 of third guard member 2240 and slits 2252' of fourth guard member 2242 are also rotationally offset from each other by 45 degrees (relative to the longitudinal axis). The rotational offset of third and fourth guard members 2240, 2242 with respect to each other provides for the plurality of curved guard portions 2241 of third guard member 2240 to span the width of slits 2252' of fourth guard member 2242, and for the plurality of curved guard portions 2241' of fourth guard member 2242 to span the width of slits 2252 of third guard member 2240.

The rotational offset of first and second guard members 2140, 2142, as well as of third and fourth guard members 2240, 2242, with respect to each other discourages unwanted contact between, and thereby facilitates the protection of, septum seal 2160 when instrument valve component 230B is disposed within the housing of a cannula assembly 200 (FIG. 6) and an instrument is inserted and/or withdrawn through orifices 2166, 2144, 2144', 2244, 2244'.

Figure 6:
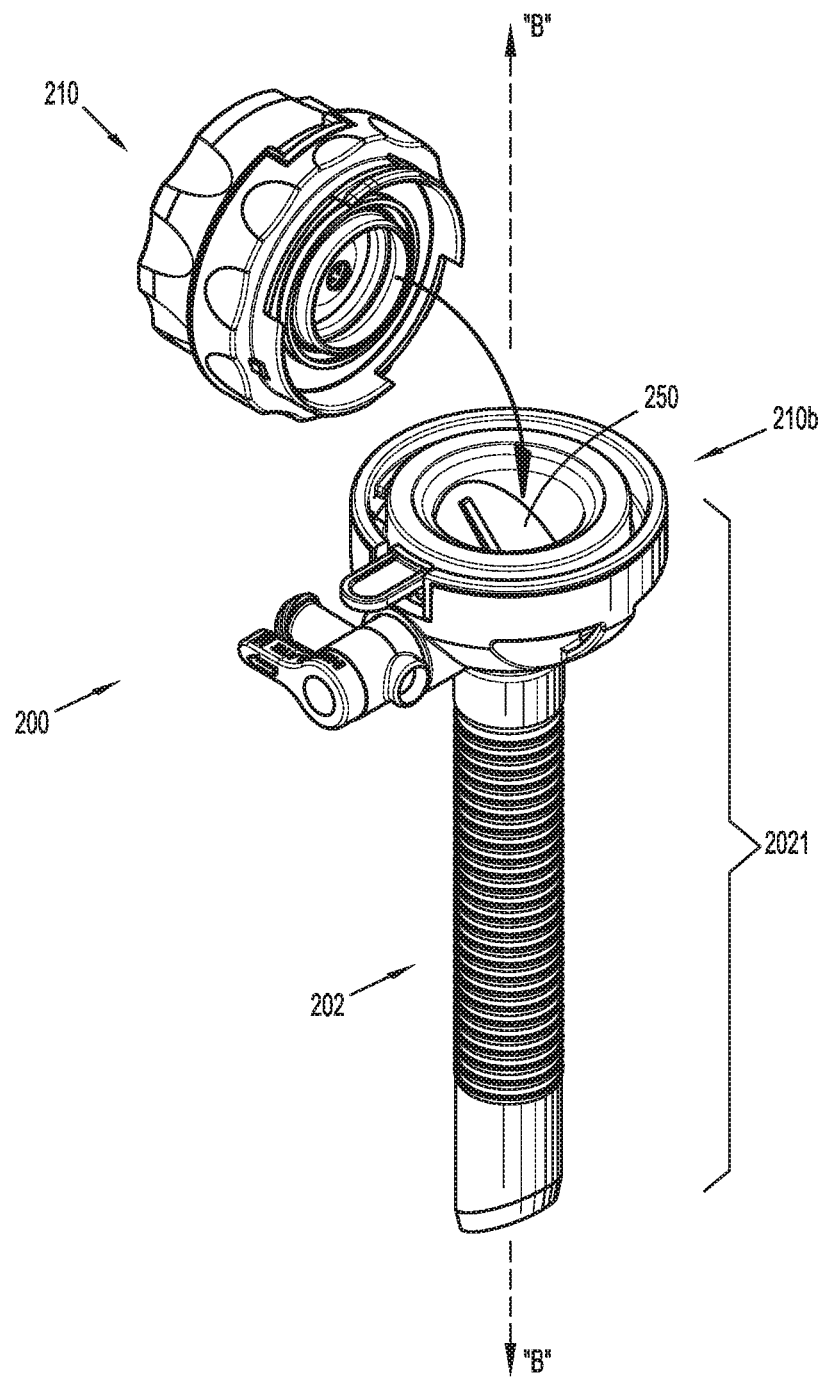
FIG. 6 is a perspective view of a cannula assembly showing a proximal housing component separated from a distal housing component.

Cannula assembly 200 will now be discussed in detail with reference to FIGS. 6-13. FIG. 6 illustrates instrument valve assembly 210 prior to its attachment to a representative distal cannula assembly, e.g., distal cannula assembly 2021. Distal cannula assembly 2021 includes an elongate tubular portion 202, defining a longitudinal axis "B-B" and a distal housing component 210b. Distal housing component 210b includes a zero-closure seal 250 that prevents the escape of insufflation gas when no instrument is present through the valve housing.

Figure 8:
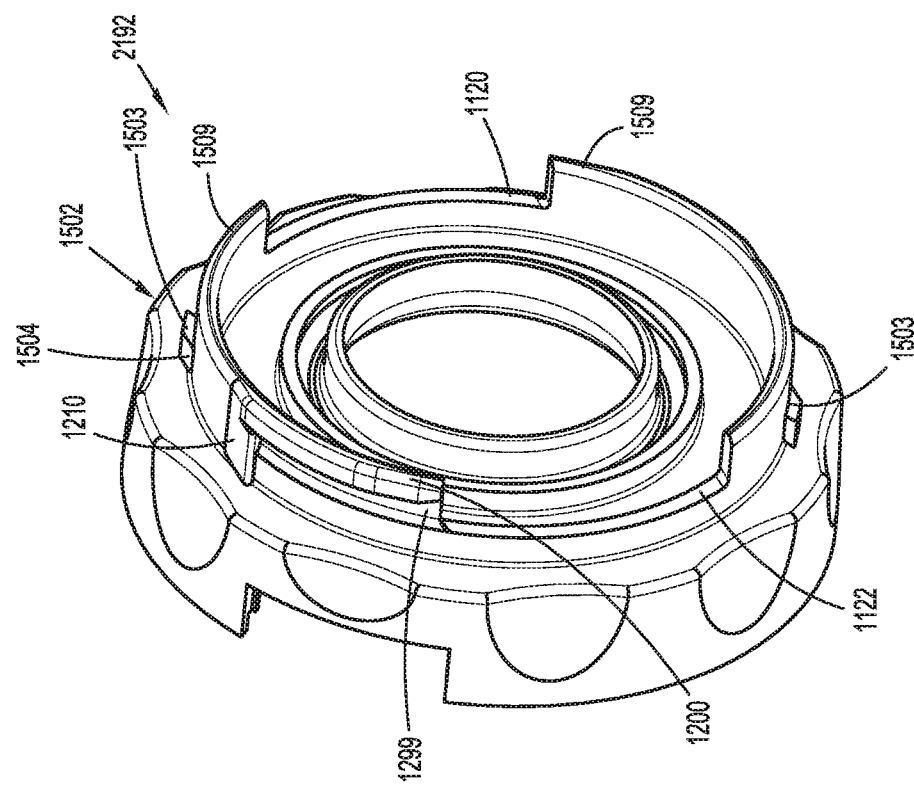
FIG. 8 is a perspective view of the proximal housing component.
Figure 7:
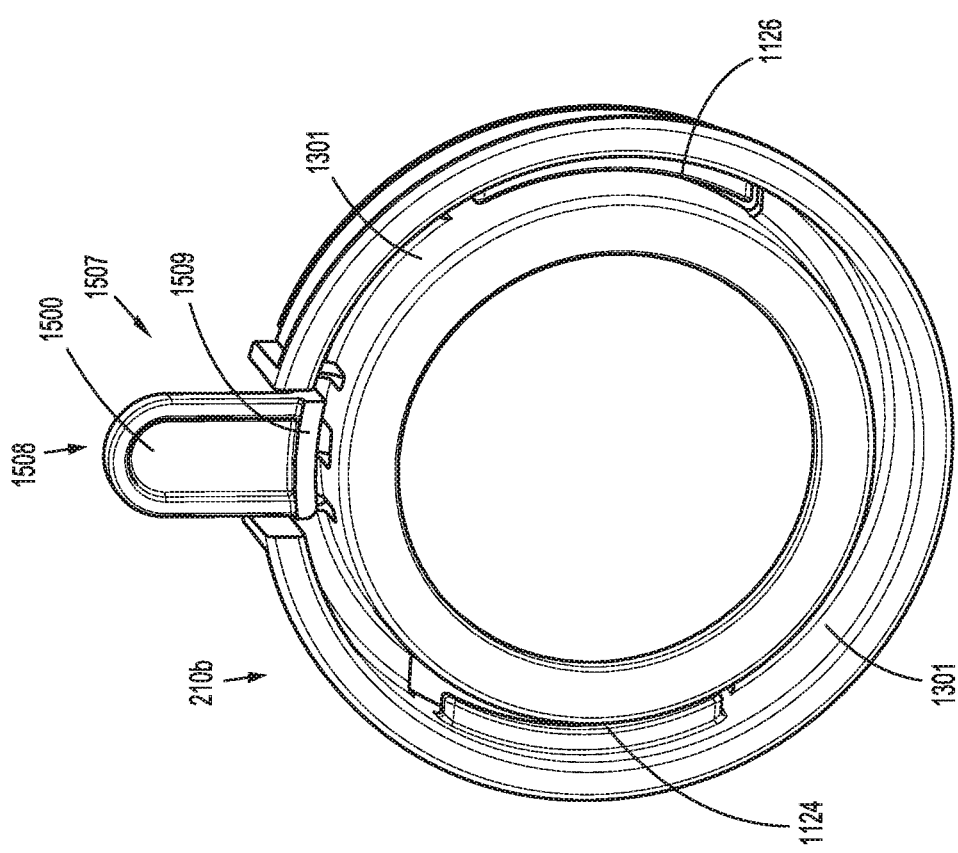
FIG. 7 is a perspective view of the distal housing component viewed from the proximal side.

As previously mentioned, the instrument valve assembly 210 may be selectively attachable to, and detachable from, distal housing component 210b. Various different types of connection mechanisms can be employed in this regard, e.g., snap-fit, latches, bayonet coupling, threaded couplings, etc. FIGS. 7-8 illustrate one such connection mechanism, and specifically illustrate additional features, according to an embodiment of the present invention, by which instrument valve assembly 210 is selectively attachable to, and detachable from, distal housing component 210b.

Referring to FIG. 7, distal housing component 210b defines annular lips 1124, 1126 located on an inner surface of an outer wall. Located circumferentially between lips 1124, 1126 is an annular channel 1301. In addition, distal housing component 210b also includes a radially outward user-actuatable portion 1508 of a rotation prevention mechanism 1500 (which will be described in greater detail below). Radially outward user-actuatable portion 1508 of rotation prevention mechanism 1500 is a tab 1507 that is integrally formed with an outer circumferential edge of distal housing component 210b. Tab 1507 further includes a radially-inward locking portion 1509. Tab 1507 is configured for resilient movement relative to distal housing component 210b about its point of attachment thereto, such that its user-actuatable portion 1508 is moveable distally relative to the circumferential edge of distal housing component 210b.

Referring to FIG. 8, second housing portion 2192 of instrument valve assembly 210 defines first and second annular recesses 1120, 1122 adjacent its distal end. Recesses 1120, 1122 are sized and shaped to receive annular lips 1124, 1126 of distal housing component 210b when distal housing component 210b and instrument valve assembly 210 are initially brought together in the axial direction. Located circumferentially between recesses 1120, 1122 of instrument valve assembly 210 are a pair of distal projections 1509. Likewise, distal projections 1509 are sized and shaped to be received by annular channel 1301 of distal housing component 210b when distal housing component 210b and instrument valve assembly 210 are initially brought together in the axial direction.

Second housing portion 2192 of instrument valve assembly 210 also has additional structures that engage with distal housing component 210b. For example, second housing portion 2192 of instrument valve assembly 210 also has structures that comprise a first component 1502 of rotation prevention mechanism 1500. These structures of instrument valve assembly 210 (e.g., the structures of first component 1502 of rotation prevention mechanism 1500) engage with the above-described structures of distal housing component 210b (e.g., the structures of radially outward user-actuatable portion 1508 of rotation prevention mechanism 1500), and enable distal housing component 210b and proximal housing component 210a, once initially brought together in the axial direction, to selectively attach and detach from each other via relative rotation of distal housing component 210b and proximal housing component 210a. For example, and referring to FIGS. 8 and 11, distal projections 1509 of instrument valve assembly 210 each include a rib 1200. Each distal projection 1509 also includes a groove 1299 located adjacent and proximal to its respective rib 1200. Additionally, each distal projection 1509 includes a stop 1210 (FIG. 8) adjacent each rib 1200. Also, distal projections 1509 include a first component 1502 of the above-referenced rotation prevention mechanism 1500. First component 1502 includes a protuberance 1503, having a ramped surface 1504 that is integrally formed on an outer circumferential surface of distal projection 1509.

Figure 9:
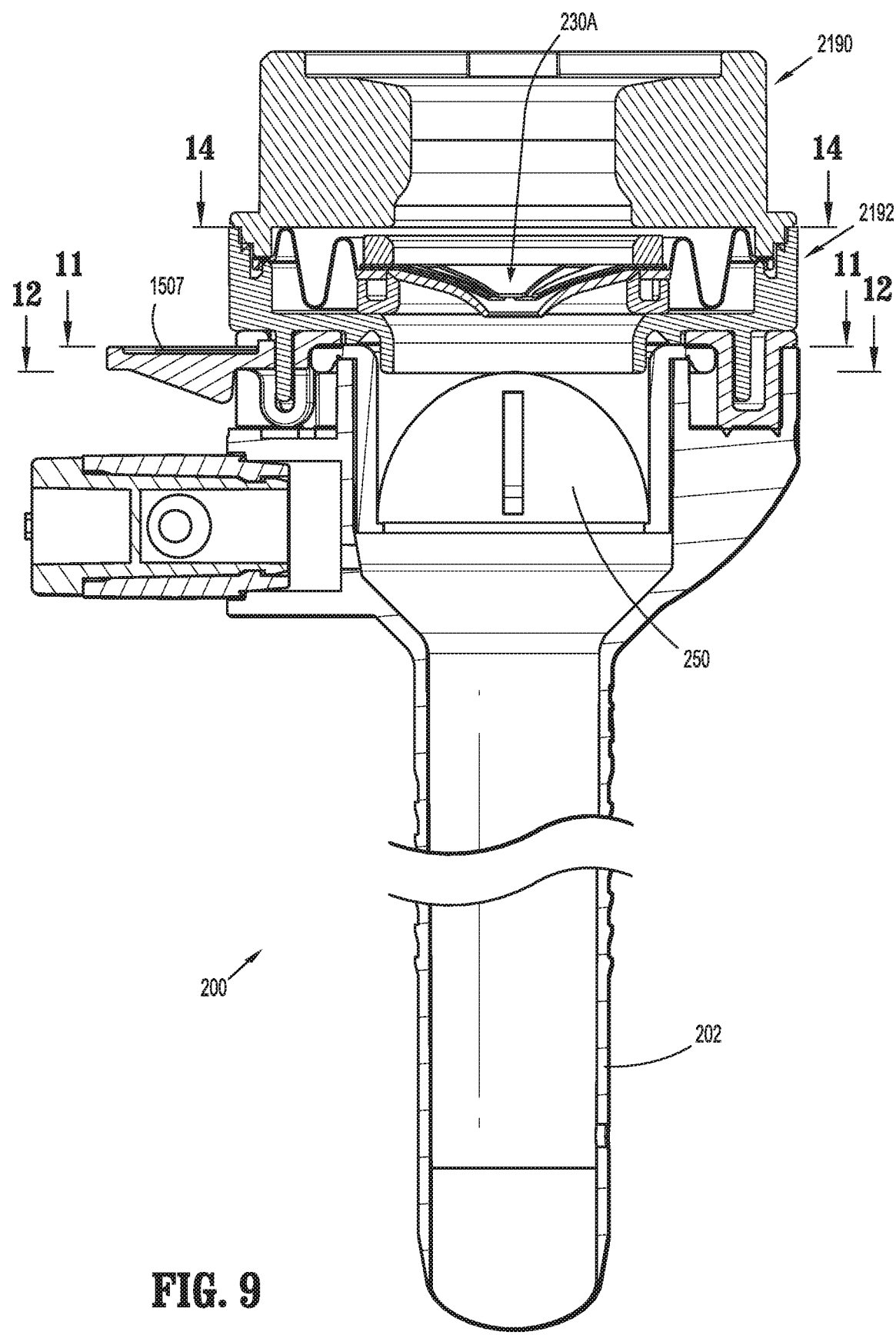
FIG. 9 is a cross-sectional view of the cannula assembly and the valve assembly of FIG. 3 illustrating the tab in a first position.
Figure 9A:
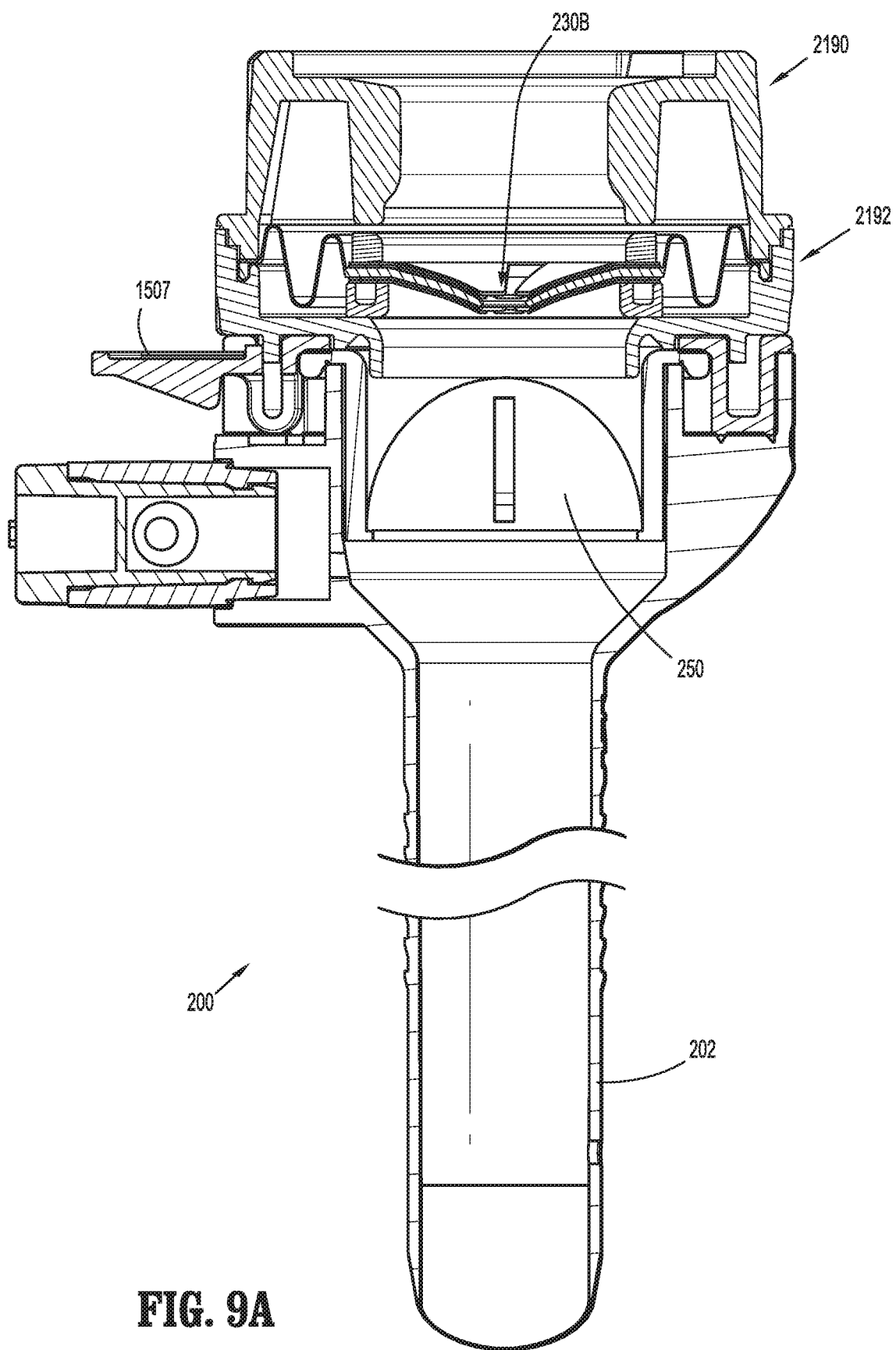
FIG. 9A is a cross-sectional view of the cannula assembly and the valve assembly of FIG. 5A illustrating the tab in a first position.
Figure 10:
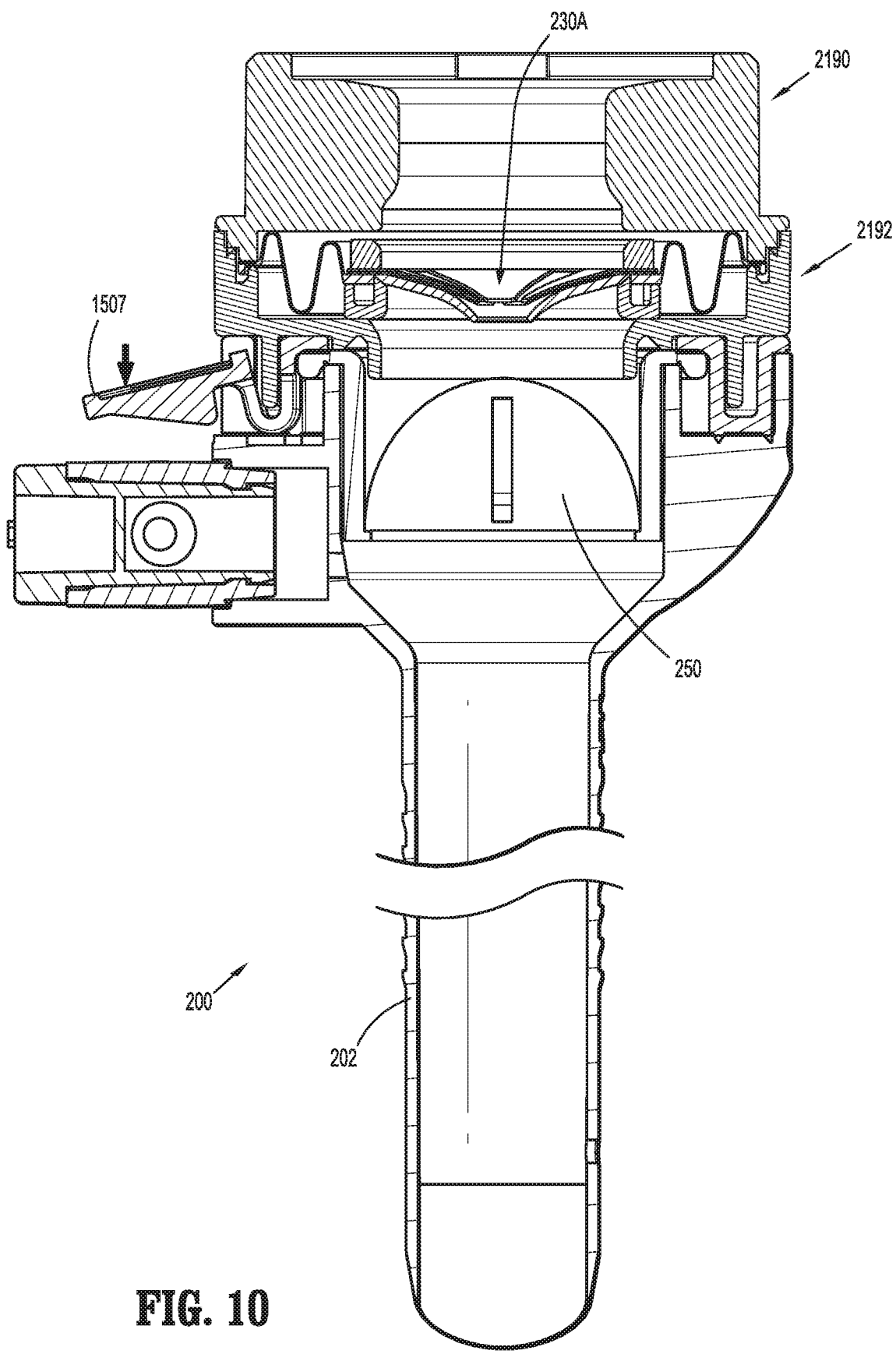
FIG. 10 is a cross-sectional view of the cannula assembly and the valve assembly of FIG. 3 illustrating the tab in a second position.
Figure 13:
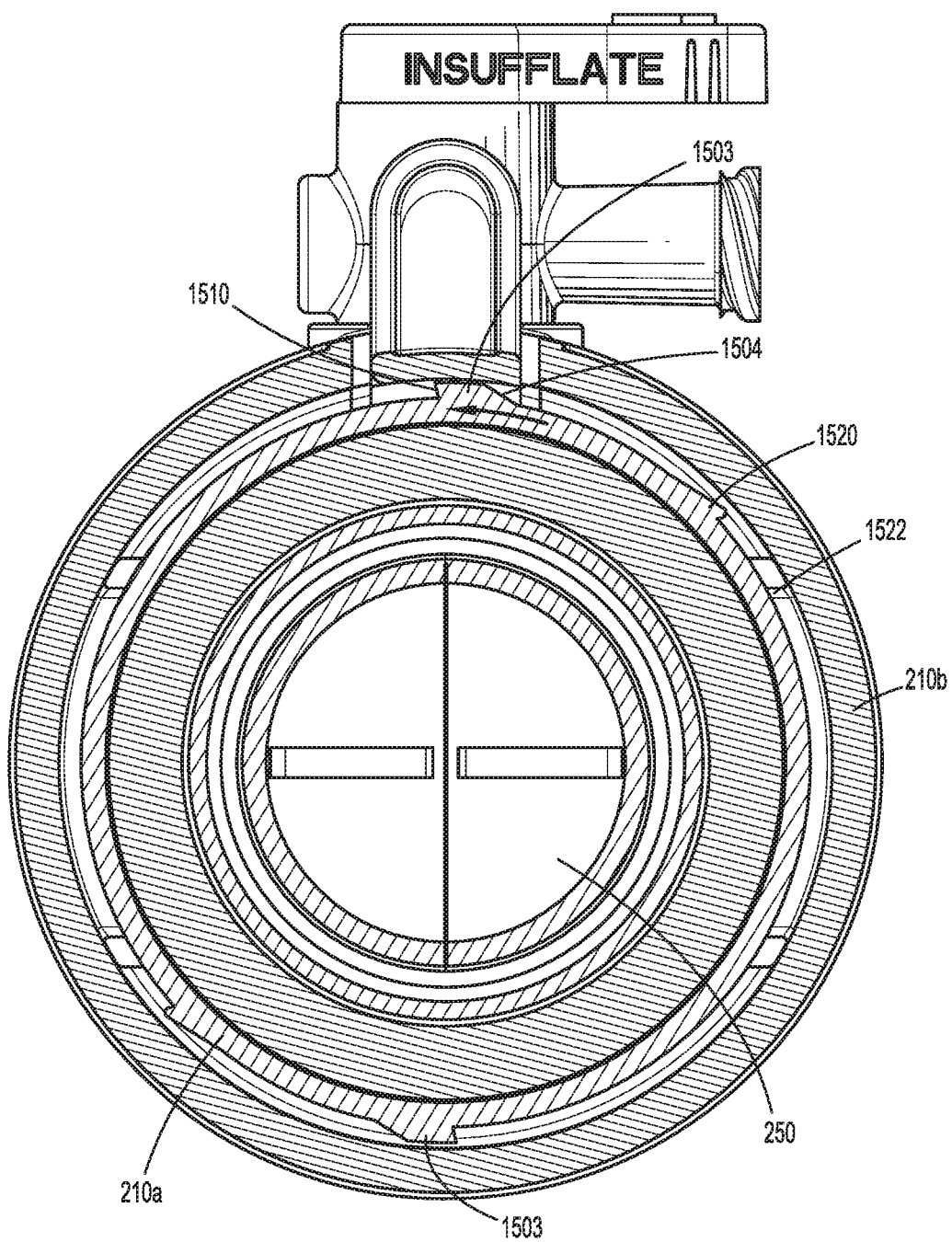
FIG. 13 is a cross-sectional view of a portion of the cannula assembly illustrating a portion of the proximal housing component engaging a portion of the distal housing component.

FIGS. 9 and 10 illustrate instrument valve assembly 210 (including first and second housing portions 2190, 2192, with instrument valve component 230A maintained therebetween) mounted on distal housing component 210b. It is noted that instrument valve component 230A may be replaced by instrument valve component 230B, as shown in FIG. 9A. In fact, instrument valve components 230A and 230B may be interchangeable throughout the exemplary embodiments described herein. In FIG. 9, tab 1507 is in a first, rest position. In this first position, relative rotation of instrument valve assembly 210 and distal housing component 210b (and thus decoupling of instrument valve assembly 210 and the distal housing component 210b) is prevented, as will be described in further detail below. In FIG. 10, tab 1507 is deflected, as by a user, into a second, actuated position. In this second position, relative rotation of instrument valve assembly 210 and distal housing component 210b (and thus decoupling of instrument valve assembly 210 and distal housing component 210b) is possible.

FIGS. 11 and 12 are cross-sectional views, taken along the lines 11-11 and 12-12, respectively, of FIG. 9, and illustrate the mating features of instrument valve assembly 210 and distal housing component 210b.

Rotation prevention mechanism 1500 prevents inadvertent relative rotation and thus potential decoupling of instrument valve assembly 210 and distal housing component 210b. Once instrument valve assembly 210 and distal housing component 210b are brought together axially, instrument valve assembly 210 may be rotated in a first direction (e.g., clockwise in the views of FIGS. 11-13), such that ramped surface 1504 of protuberance 1503 engages the locking portion 1509 of tab 1507. Continued rotation of instrument valve assembly 210 causes protuberance 1503 to exert a force directed in the radially outward direction on locking portion 1509 of tab 1507. The radially outward force is sufficient to cause tab 1507 to move radially outward relative to the circumferential edge of distal housing component 210b about its point of attachment thereto, from its first position towards its second position. Additionally, the radially outward force causes the user actuatable portion 1508 of tab 1507 to move distally. After a predetermined amount of rotation of proximal housing component 210a, protuberance 1503 passes tab 1507, and causes locking portion 1509 of tab 1507 to move back to its first position and adjacent to a perpendicular surface 1510 (FIGS. 11 and 13) of protuberance 1503. In this position, instrument valve assembly 210 is effectively prevented from counter-clockwise rotation with respect to distal housing component 210b.

Additionally, when sufficient rotation of instrument valve assembly 210 causes protuberance 1503 to pass tab 1507, protrusion 1520 (FIGS. 11 and 13) of instrument valve assembly 210 contacts a stop 1522 (FIGS. 11 and 13) of distal housing component 210b, thus effectively preventing additional clockwise rotation between instrument valve assembly 210 and distal housing component 210b. Accordingly, in the relative position of instrument valve assembly 210 and distal housing component 210b illustrated in FIG. 11, both directions of rotation of instrument valve assembly 210 are effectively prevented, and thus instrument valve assembly 210 is rotationally fixed with respect to distal housing component 210b. Annular lips 1124, 1126 of distal housing component 210b are positioned within the respective grooves 1299 of the distal projections of instrument valve assembly 210, and are maintained in the grooves by ribs 1200, thereby also preventing instrument valve assembly 210 and distal housing component 210b from moving axially relative to each other. In this manner, rotation prevention mechanism 1500 prevents instrument valve assembly 210 from inadvertently rotating relative to, and thus inadvertently becoming disconnected from distal housing component 210b once instrument valve assembly 210 reaches this locked position.

To remove instrument valve assembly 210 from distal housing component 210b, a user exerts a force on tab 1507 directed in the distal direction, as shown in FIG. 10. A sufficient amount of distally-directed force causes the user actuatable portion 1508 of tab 1507 to move distally relative to the circumferential edge of distal housing component 210*b* about its point of attachment thereto until locking portion 1509 of tab 1507 is located radially outward of protuberance 1503. In this position, instrument valve assembly 210 is no longer prevented from rotating, but rather is free to rotate, in a second direction (e.g., counter-clockwise as shown by the arrow in FIG. 13) relative to distal housing component 210*b*. In this manner, rotation prevention mechanism 1500 provides a selectively actuatable mechanism that, when actuated, enables a user to rotate and thereby disconnect instrument valve assembly 210 from distal housing component 210*b*.

Figure 14:
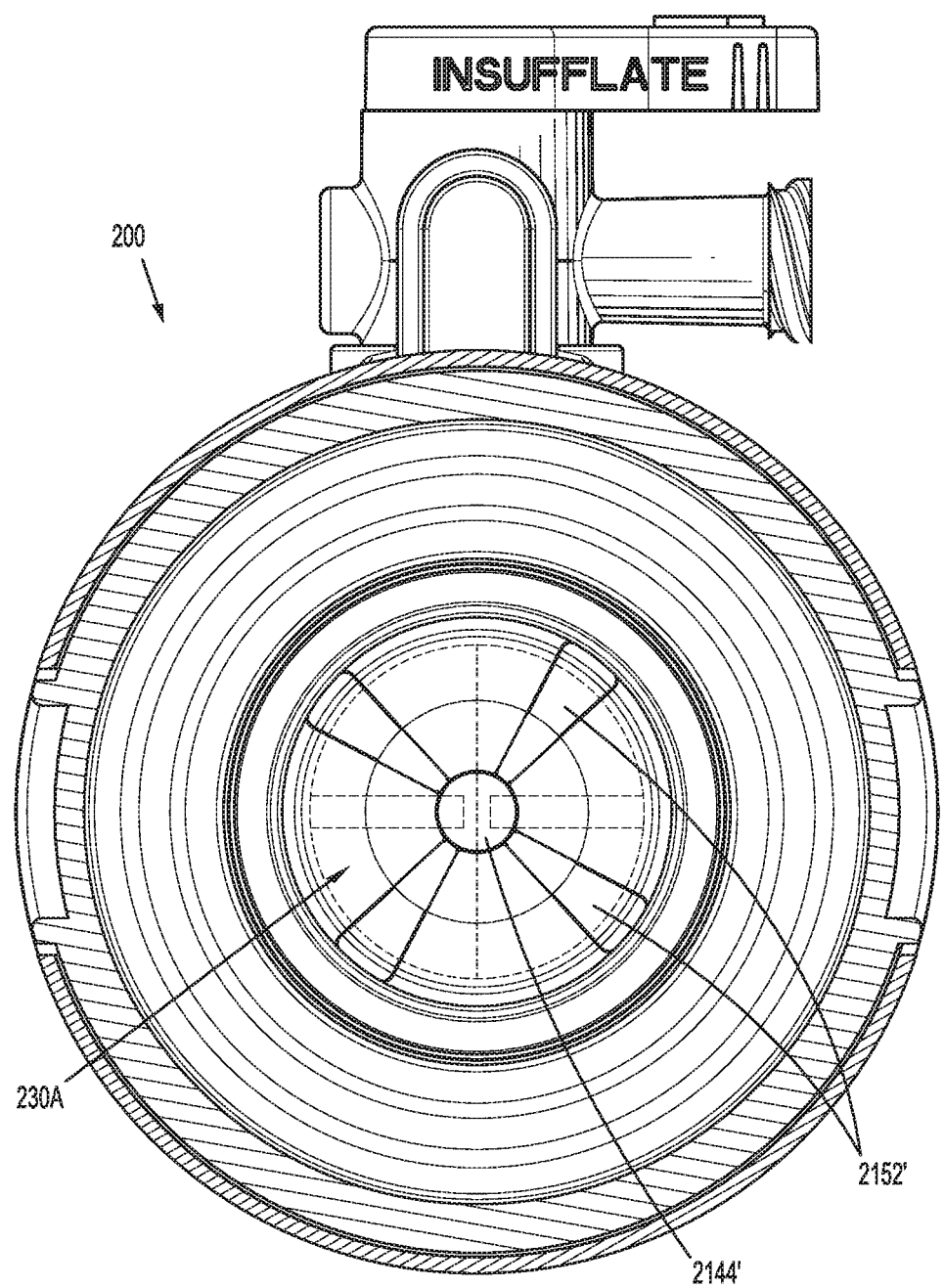
FIG. 14 is a cross-sectional view of a portion of the cannula assembly illustrating the valve assembly radially centered within the housing taken along line 14-14 in FIG. 9.
Figure 15:
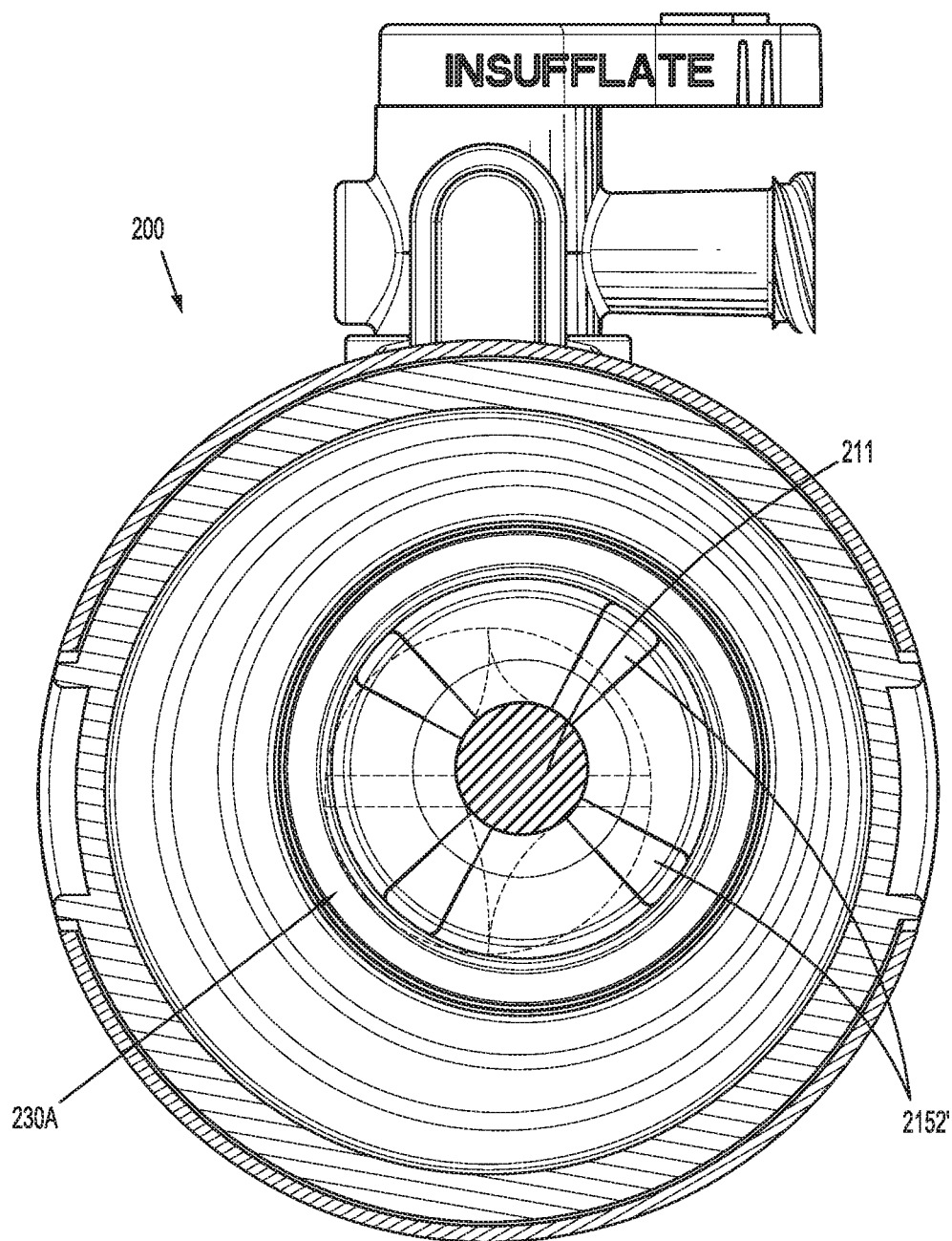
FIG. 15 is a cross-sectional view of a portion of the cannula assembly illustrating an instrument inserted through the valve assembly, and the valve assembly being rotationally offset within the housing.

FIGS. 14 and 15 illustrate the operation of the instrument valve assembly 210 in use during surgery. FIG. 14 illustrates instrument valve assembly 210 in a rest position, while FIG. 15 illustrates instrument valve assembly 210 having a surgical instrument 211 inserted therethrough in an off-axis position. As shown in FIG. 15, when an instrument is moved through instrument valve assembly 210, the elastomeric material of septum seal 2160 is protected by the first and second guard members 2140, 2142. For example, because the width of each one of the plurality of curved guard portions 2141 of first guard member 2140 is wider than slits 2152' of second guard member 2142 when instrument valve component 230A is in the rest position, movement of instrument 211 through orifice 2166 of septum seal 2160 insures that at least one of the plurality of curved guard portions 2141 of first guard member 2140 prevents instrument 211 from tearing seal 2160 directly beneath slits 2152'. As noted above, instrument valve component 230B may be substituted for instrument valve component 230A. In fact, instrument valve components 230A and 230B may be interchangeable throughout the exemplary embodiments described herein.

Likewise, because the width of each one of the plurality of curved guard portions 2141' of second guard member 2142 is wider than slits 2152 of first guard member 2140 when instrument valve component 230A is in the rest position, movement of instrument 211 through orifice 2166 of septum seal 2160 insures that the instrument contacts at least one of the plurality of curved guard portions 2141' of second guard member 2142 rather than directly contacting, and potentially tearing, the elastomeric material of septum seal 2160 directly beneath the slits 2152. Still further, the width of each one of the plurality of curved guard portions 2141, 2141' is sufficiently greater than the respective slits 2152, 2152' which they span, such that as the curved guard portions 2141, 2141' spread apart as an instrument is inserted therethrough, thereby widening the slits 2152, 2152', as well as still cover their respective slits 2152, 2152'. This reduces the likelihood that an inserted instrument will inadvertently contact and tear the elastomeric material of the seal and allows the arrangement to accommodate a variety of different sized instruments.

In addition, by virtue of the bellows arrangement, orifice 2166 of septum seal 2160 may be moved to an off-center location (FIG. 15) with minimal force, thereby reducing the likelihood that the elastomeric material of septum seal 2160 directly around orifice 2166 is caused to cat-eye and leak by such off-axis movement. In addition, upon removal of the instrument, the bellowed arrangement helps to urge orifice 2166 back towards the radial center of instrument valve component 230A, such that orifice 2166 is in a centered location for reception of a subsequently-inserted surgical instrument. Urging orifice 2166 back towards the radial center of instrument valve component 230A prior to reception of a subsequently-inserted surgical instrument increases the likelihood that the subsequently-inserted surgical instrument is received by orifice 2166 and reduces the likelihood that the subsequently-inserted surgical instrument tears the elastomeric material of septum seal 2160.

As set forth above, various different types of obturators, e.g., bladed, bladeless, blunt, optical, non-optical, etc. may be employed in the trocar assemblies of the present invention. Several of these types are described in additional detail hereinbelow, although it should be recognized that various other types of obturators may be employed, e.g., obturators having structure, e.g., tip geometries, other than those shown.

Figure 16:
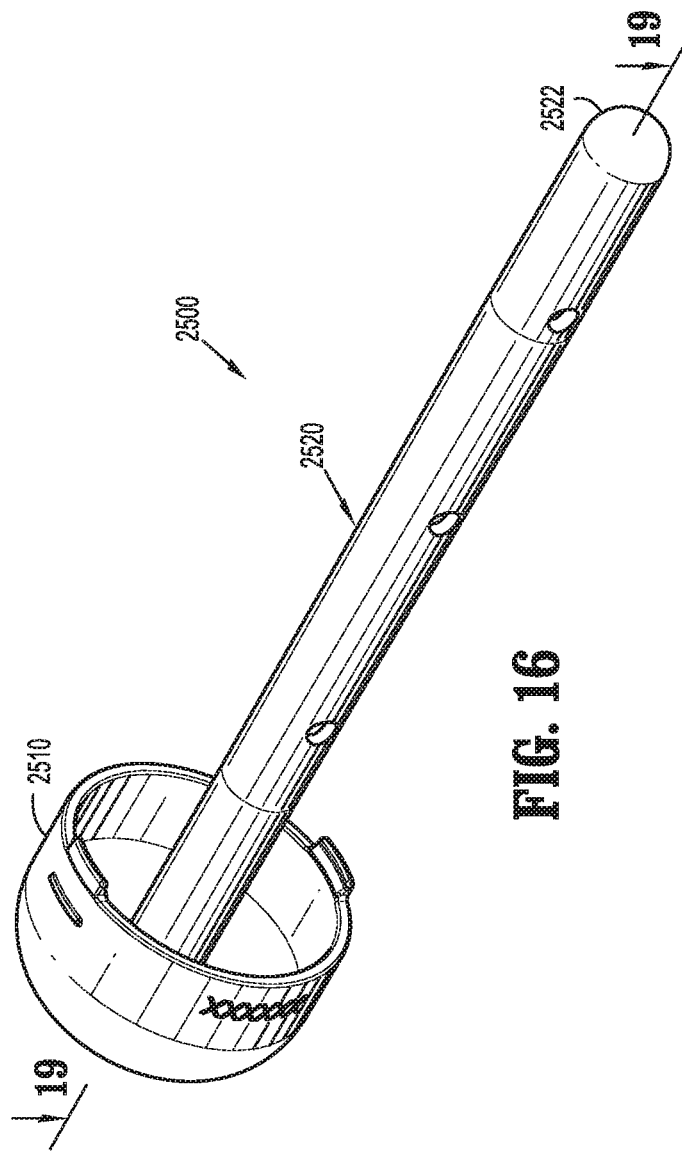
FIG. 16 is a perspective view of a first embodiment of an obturator for separating tissue planes in an endoscopic surgical procedure.
Figure 17:
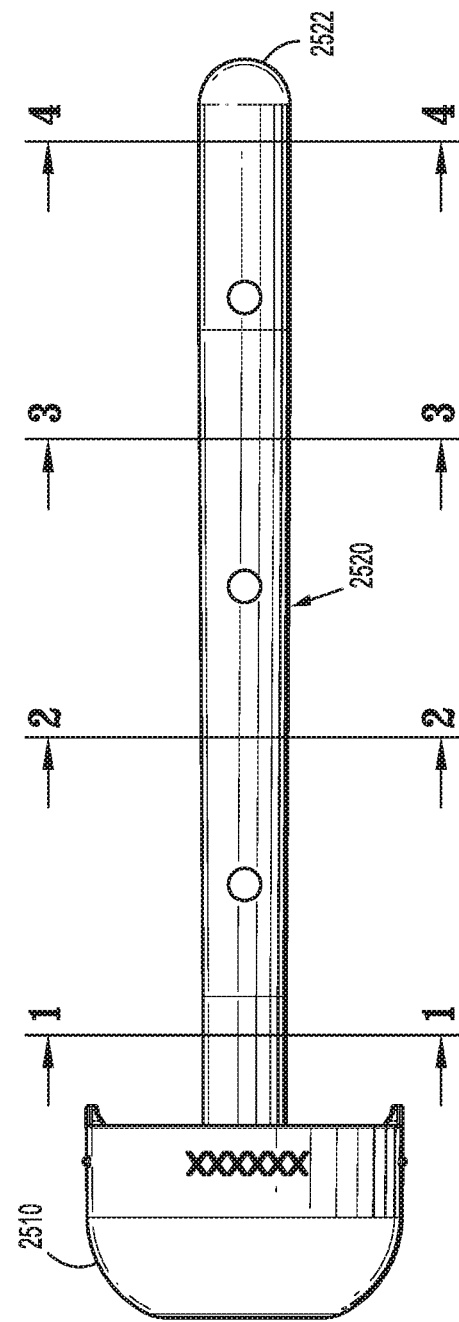
FIG. 17 is a side view of the obturator of FIG. 16.

Referring to FIGS. 16-21, a first example embodiment of a blunt obturator for separating tissue planes in an endoscopic surgical procedure is shown and described. With reference to FIGS. 16 and 17, obturator 2500 includes an obturator housing 2510 and an elongate shaft 2520. Elongate shaft 2520 includes a proximal end, a distal end, and a tubular member therebetween. Proximal end of elongate shaft 2520 may be connected, e.g., snap-fit, welded, etc., to obturator housing 2510 and extends proximally out of the proximal end of a cannula housing 2504 (FIG. 21) when obturator 2500 is fully positioned therewithin. The distal end of elongate shaft 2520 extends distally out of a distal end 2502*a* of a cannula tube 2502 (FIG. 21) when obturator 2500 is positioned therewithin. The distal end of elongate shaft 2520 includes a member 2522 that closes the distal end of elongate shaft 2520. Member 2522 is adapted for blunt tissue dissection and includes a hemispherical outer surface that functions to help separate tissue along natural tissue planes. The hemispherical outer surface of the distal end defines a radius of curvature dimensioned to be atraumatic to tissue. Elongate shaft 2520 and member 2522 are monolithically fabricated from any suitable material such as an acrylonitrile butadiene styrene plastic material ("ABS") that may be opaque. Obturator housing 2510 and/or member 2522 may additionally or alternatively be fabricated from a material that is transparent or translucent.

FIGS. 17A-17D delineate cross-sections of elongate shaft 2520 as taken through the plurality of corresponding section lines. FIGS. 17A-17D illustrate the cross-sections taken along lines 1-1, 2-2, 3-3, and 4-4 through elongate shaft 2520 are circular.

Figure 18:
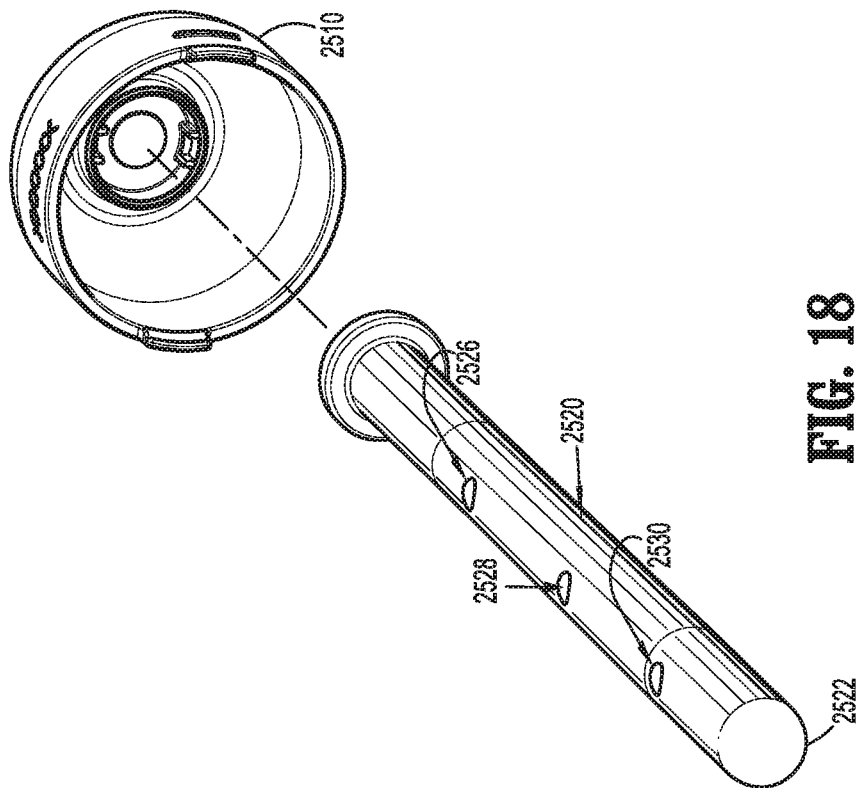
FIG. 18 is a perspective view of the obturator with parts separated.
Figure 17A:
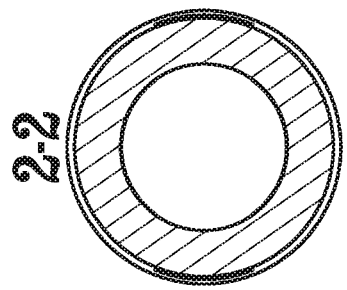
FIGS. 17A-17D show cross-sections of the elongate shaft taken along lines 1-1, 2-2, 3-3, and 4-4 of the obturator of FIG. 16.
Figure 17B:
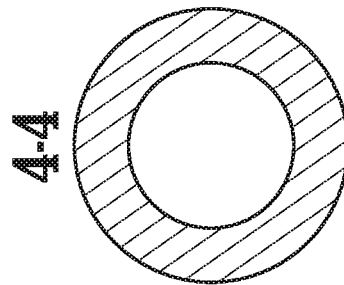
Figure 17C:
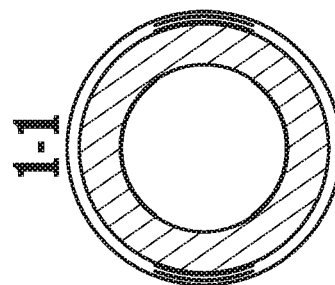
Figure 17D:
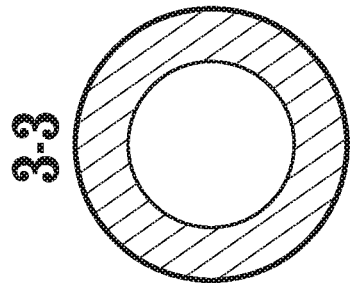

With reference to FIGS. 18-20, elongate shaft 2520 has an inner surface 2520*a* and an outer surface 2520*b* that define an outer wall 2520*c*. Inner surface 2520*a* defines a central bore 2524 that extends through the tubular member from the proximal end of elongate shaft 2520 to an arcuate surface 2520*d* at a distal end of inner surface 2520*a*.

Figure 21:
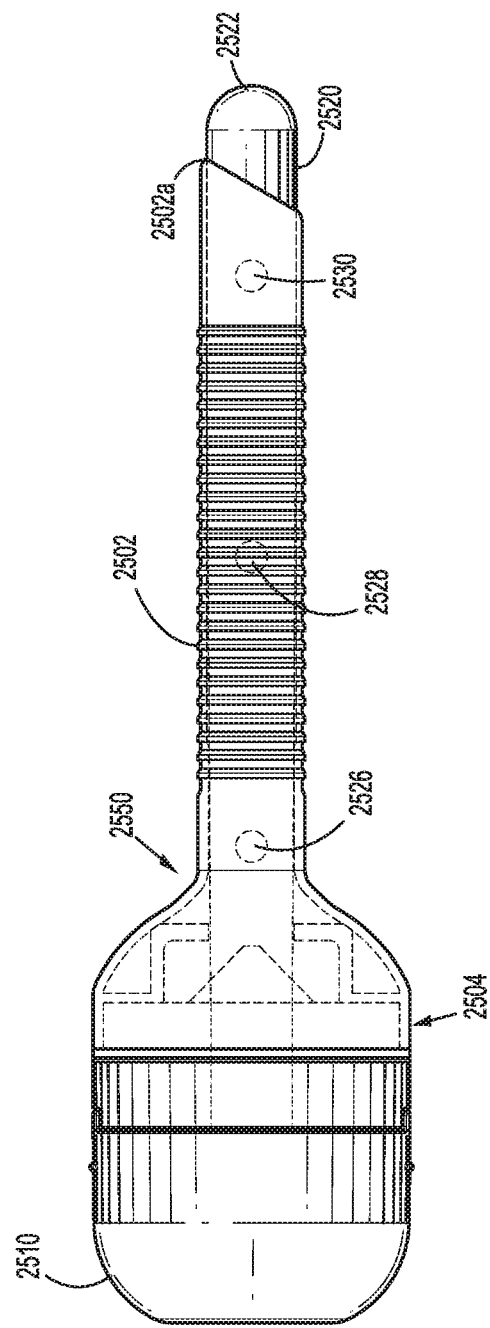
FIG. 21 is a side view of the obturator of FIG. 16 inserted through a cannula.

The tubular portion of elongate shaft 2520 includes a pair of proximal apertures 2526, a pair of intermediate apertures 2528, and a pair of distal apertures 2530. Each aperture 2526, 2528, and 2530 extends through inner and outer surfaces 2520*a*, 2520*b* of elongate shaft 2520. When obturator 2500 is fully positioned within cannula 2550, apertures 2526, 2528, and 2530 are all positioned within, and covered by, cannula tube 2502 of cannula 2550 (FIG. 21).

In operation, member 2522 enables initial insertion of obturator 2500 within an opening in tissue, e.g., a pre-cut scalpel incision. Member 2522 facilitates advancement of obturator 2500 between tissue layers to gently dissect tissue and enlarge the opening without any cutting or incising of the tissue.

As illustrated above in FIG. 21, obturator 2500 is disposed within a cannula 2550. Cannula 2550 includes cannula tube 2502 extending distally from cannula housing 2504. Obturator housing 2510 is releasably coupled to cannula housing 2504. When obturator 2500 is coupled to cannula 2550, a portion of elongate shaft 2520 and member 2522 extend distally beyond distal end 2502a of cannula tube 2502. Each of the apertures (2526, 2528, and 2530) is positioned within cannula tube 2502 and proximal of distal end 2502a of cannula tube 2502.

Referring to FIGS. 22-30, a second embodiment of an obturator for separating tissue planes in an endoscopic surgical procedure is presented.

Figure 26:
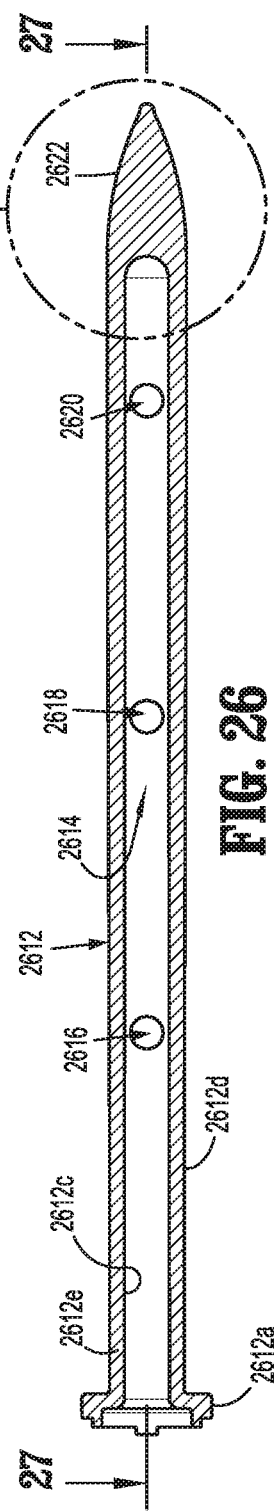
FIG. 26 is a cross-sectional view of the obturator of FIG. 22.
Figure 27:
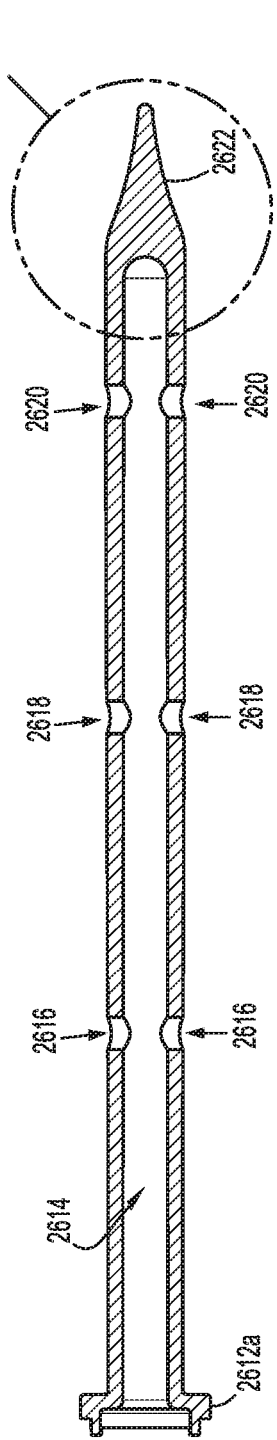
FIG. 27 is a cross-sectional view of the obturator of FIG. 26 rotationally offset by 90 degrees, taken along section line 27-27.
Figure 28:
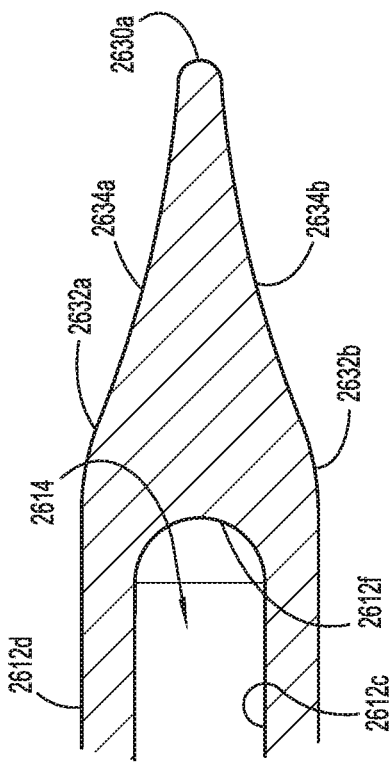
FIG. 28 is an enlarged cross-sectional view of the distal portion of the elongate shaft of the obturator of FIG. 22.
Figure 29:
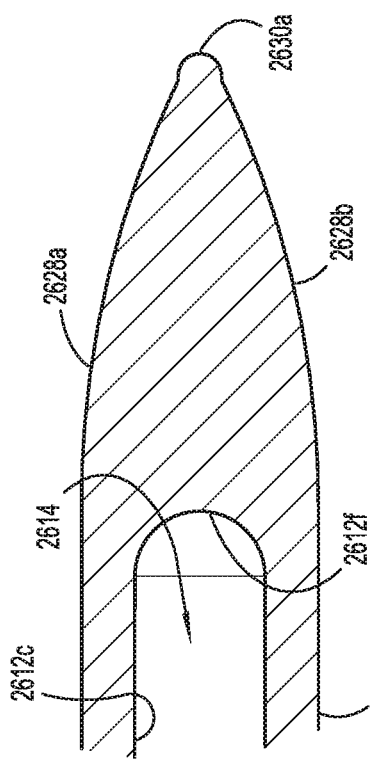
FIG. 29 is an enlarged cross-sectional view of the distal portion of the elongate shaft of the obturator of FIG. 27.

With reference to FIG. 22, obturator 2600 includes an elongate shaft 2612 having a proximal end 2612a, a distal end 2612b, and a tubular member extending therebetween. Although not shown in these figures, the obturator 2600 may also include a handle or housing, e.g., like the housing of 2510 of the obturator 2500. Referring additionally to FIG. 26, elongate shaft 2612 includes an inner surface 2612c and an outer surface 2612d that define an outer wall 2612e. With reference also to FIGS. 28 and 29, a bore 2614 originates at proximal end 2612a and extends into elongate shaft 2612 to an arcuate surface 2612f (FIG. 28) at a distal end of inner surface 2612c.

Figure 30:
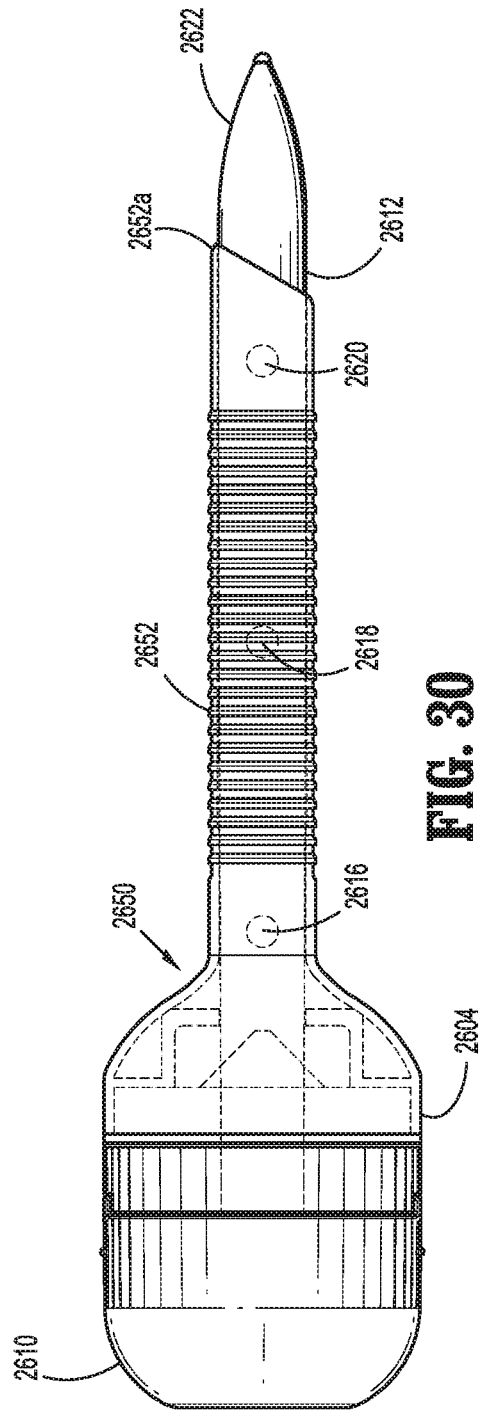
FIG. 30 is side view of the obturator of FIG. 22 inserted through a cannula.

With reference again to FIGS. 26 and 27, the tubular portion of elongate shaft 2612 includes a pair of proximal apertures 2616, a pair of intermediate apertures 2618, and a pair of distal apertures 2620. Each aperture 2616, 2618, and 2620 extends through inner and outer surfaces 2612c, 2612d of elongate shaft 2612. When obturator 2600 is fully positioned within cannula 2650, apertures 2616, 2618, and 2620 are all positioned within, and covered by, cannula tube 2602 of cannula 2650 (FIG. 30).

Referring again to FIG. 23, a distal portion of elongate shaft 2612 includes a member 2622. Elongate shaft 2612 and member 2622 may be monolithically fabricated from any suitable material such as an acrylonitrile butadiene styrene plastic material ("ABS") that may be opaque. Elongate shaft 2612 and/or member 2622 may additionally or alternatively be fabricated from a material that is transparent or translucent.

Figure 24:
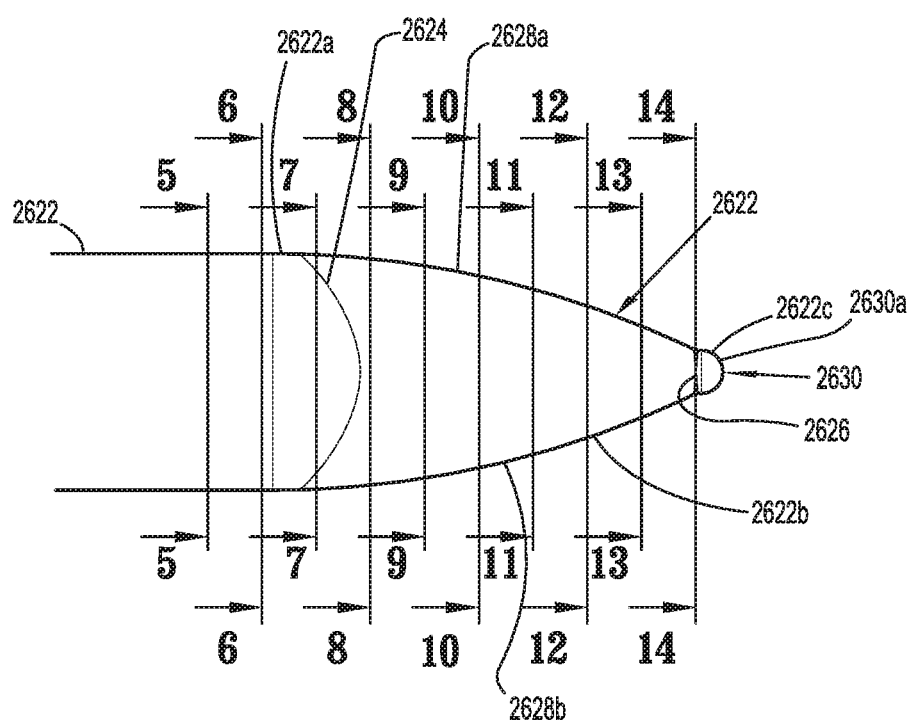
FIG. 24 is an enlarged top view of the distal portion of the elongate shaft of FIG. 23.
Figure 24A:
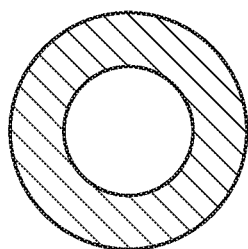
FIGS. 24A-24J show cross-sections of the distal portion taken along lines 5-5, 6-6, 7-7, 8-8, 9-9, 10-10, 11-11, 12-12, 13-13, and 14-14.
Figure 24B:
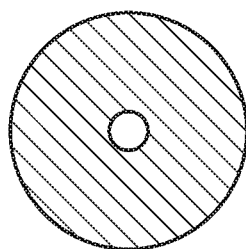
Figure 24C:
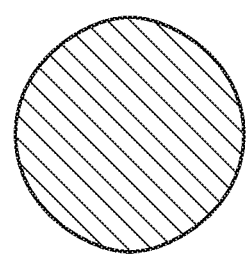
Figure 24D:
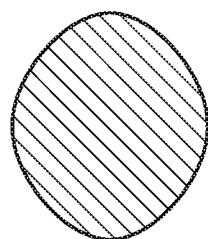
Figure 24E:
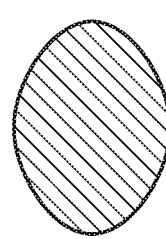
Figure 24F:
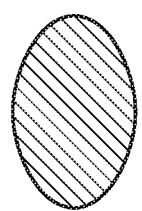
Figure 24G:
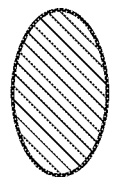
Figure 24H:
Figure 24I:
Figure 24J:
Figure 25:
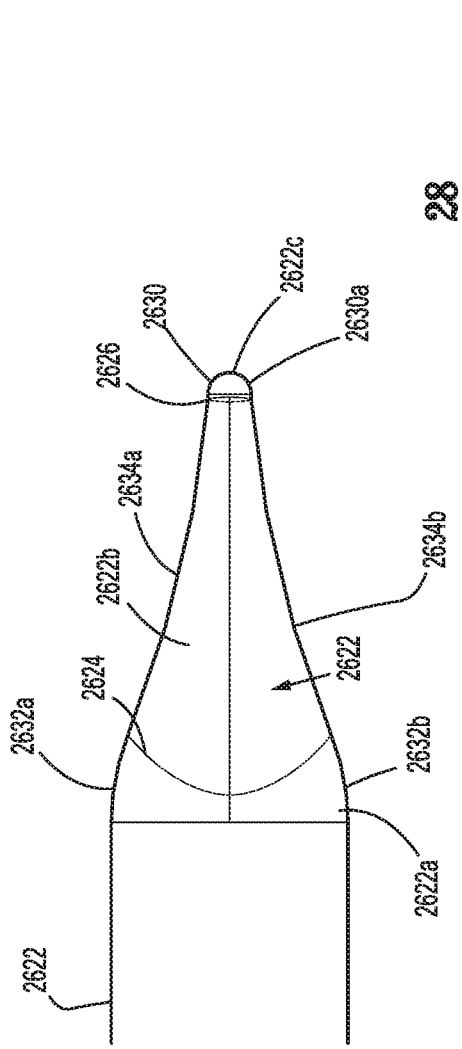
FIG. 25 is an enlarged top view of the distal portion of the elongate shaft of FIG. 24 rotationally offset by 90 degrees.

Referring to FIG. 24, an enlarged top view of the distal portion of elongate shaft 2612 is illustrated. This top view is rotationally offset 90 degrees relative to an enlarged side view of a distal portion of elongate shaft 2612 depicted in FIG. 25. As seen in FIGS. 24 and 25, member 2622 includes a proximal section 2622a, a central section 2622b, and an atraumatic guiding nub 2622c. An imaginary line 2624 (shown to illustrate curvature) separates proximal section 2622a and central section 2622b. Similarly, an imaginary line 2626 (shown to illustrate curvature) separates central section 2622b and atraumatic guiding nub 2622c.

Central section 2622b extends distally from proximal section 2622a such that, together, proximal and central section's 2622a, 2622b include a pair of diametrically opposed outer surfaces 2628a, 2628b. Each of opposed outer surfaces 2628a, 2628b is generally convex. Atraumatic guiding nub 2622c extends distally from central section 2622b and includes a rounded end 2630. Rounded end 2630 defines a radius of curvature dimensioned to be atraumatic to tissue. More specifically, rounded end 2630 includes rounded outer surfaces 2630a that function to help separate tissue along natural tissue planes. Proximal section 2622a includes a pair of diametrically opposed outer surfaces 2632a, 2632b. Each of opposed outer surfaces 2632a, 2632b is generally convex. Central section 2622b includes a pair of diametrically opposed concave outer surfaces 2634a, 2634b that are positioned between the pair of diametrically opposed outer surfaces 2632a, 2632b of proximal section 2622a and rounded outer surfaces 2630a of rounded end 2630.

FIGS. 24A-24J delineate a plurality of lines of cross-section. FIGS. 24A-24J show the cross-sections taken along lines 5-5 and 6-6 of distal portions of elongate shaft 2612, which are circular, the cross-sections taken along lines 7-7 of proximal section 2622a and 8-8 of central section 2622b, which are generally circular or irregular shape, the cross-sections taken along lines 9-9, 10-10, 11-11, 12-12, and 13-13 of central section 2622b, which are oval or generally oval shapes, and the cross-section taken along line 14-14 through atraumatic guiding nub 2622c, which is circular. The length from cross-section 9-9 through cross-section 13-13 is less than one-half of the overall length of the member 2622. Thus, the majority of the length of member 2622 is either circular or irregularly shaped.

In operation, atraumatic guiding nub 2622c enables initial insertion of obturator 2600 within an opening in tissue, e.g., a pre-cut scalpel incision, and facilitates advancement of member 2622 between tissue layers to gently dissect tissue without any cutting or incising of the tissue. After initial insertion and continued distal insertion, central section 2622b and proximal section 2622a continue to gently enlarge the opening in tissue.

As illustrated above in FIG. 30, obturator 2600 is disposed within a cannula 2650. Cannula 2650 includes cannula tube 2652 extending distally from cannula housing 2604. Obturator housing 2610 is releasably coupled to cannula housing 2604. When obturator 2600 is coupled to cannula 2650, a portion of elongate shaft 2612 and member 2622 extend distally beyond distal end 2652a of cannula tube 2652. Each of the apertures (2616, 2618, and 2620) is positioned within cannula tube 2652 and proximal of distal end 2652a of cannula tube 2652. Obturator housing 2610 may be made from any suitable material such as ABS and may be opaque and may be welded to elongate shaft 2612.

Referring to FIGS. 31-37, a third embodiment of an obturator for separating tissue planes in an endoscopic surgical procedure is presented.

With reference to FIGS. 31 and 32, obturator 2700 includes an obturator housing 2710 and an elongate shaft 2720. Elongate shaft 2720 includes a proximal end, a distal end, and a tubular member extending therebetween. The proximal end of elongate shaft 2720 may be welded or otherwise fixedly attached to obturator housing 2710 and extends proximally out of the proximal end of a cannula housing 2704 (FIG. 37) when the obturator is fully positioned therewithin. The distal end of elongate shaft 2720 extends distally out of a distal end 2752a of a cannula tube 2752 (FIG. 37) when the obturator is positioned therewithin. The distal end of elongate shaft 2720 includes a member 2722 that closes the distal end of elongate shaft 2720. Member 2722 is adapted for blunt tissue dissection. Elongate member 2720 and member 2722 may be monolithically fabricated from any suitable material such as acrylonitrile butadiene styrene plastic material ("ABS") that may be opaque. Obturator housing 2710 may be fabricated from any suitable material such as ABS that may be opaque. Member 2722 includes a proximal section 2722a and a rounded tip 2722b that extends distally from proximal section 2722a. Proximal section 2722a has a frustoconical shape. Rounded tip 2722b includes rounded outer surfaces that function to help separate tissue along natural tissue planes and define a radius of curvature dimensioned to be atraumatic to tissue.

FIG. 33 is an enlarged side view illustrating a distal end portion of elongate shaft 2720 including member 2722.

FIGS. 33A-33F illustrate cross-sections of elongate shaft 2720 as taken through the plurality of corresponding section lines. In particular, the cross-sections taken along lines 1-1, 2-2, 3-3, 4-4, 5-5, and 6-6 through member 2722 of elongate shaft 2720 are circular.

With reference to FIGS. 34-36, elongate shaft 2720 has an inner surface 2720*a* and an outer surface 2720*b* that define and outer wall 2720*c*. Inner surface 2720*a* defines a central bore 2724 that extends through the tubular member from the proximal end of elongate shaft 2720 to a frustoconcial surface 2720*d* having an arcuate end surface 2720*e* at a distal end of inner surface 2720*a*.

Figure 37:
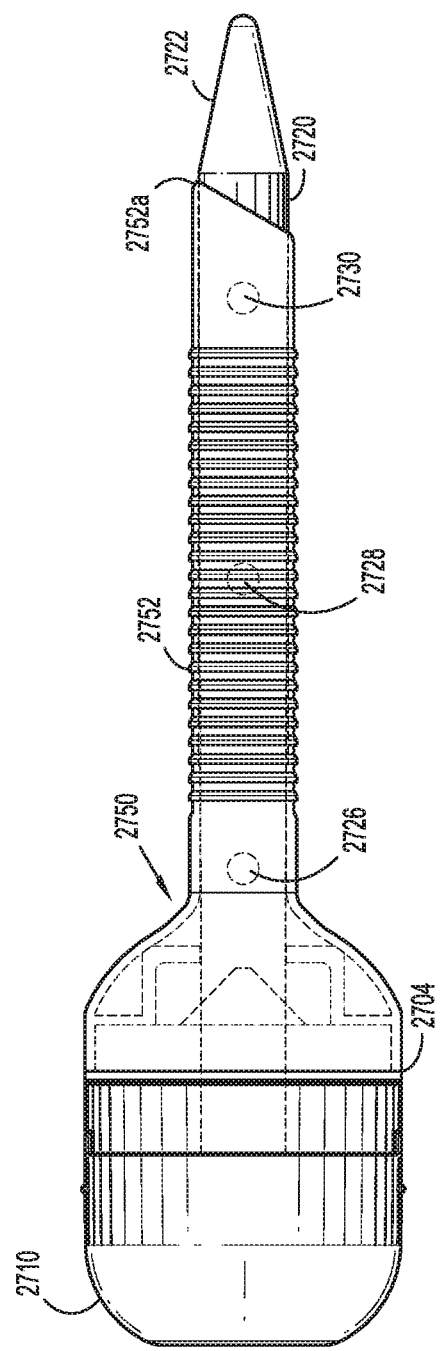
FIG. 37 is side view of the obturator of FIG. 31 inserted through a cannula.

The tubular portion of elongate shaft 2720 includes a pair of proximal apertures 2726, a pair of intermediate apertures 2728, and a pair of distal apertures 2730. Each aperture 2726, 2728, and 2730 extends through inner and outer surfaces 2720*a*, 2720*b* of elongate shaft 2720. When obturator 2700 is fully positioned within cannula 2750, apertures 2726, 2728, and 2730 are all positioned within, and covered by, cannula tube 2752 of cannula 2750 (FIG. 37).

In operation, rounded tip 2722*b* enables initial insertion of obturator 2700 within an opening in tissue, e.g., a pre-cut scalpel incision, and facilitates advancement of member 2722 between tissue layers to gently dissect tissue without any cutting or incising of the tissue. After initial insertion and continued distal insertion, proximal section 2722*a* continues to gently enlarge the opening in tissue.

As illustrated below in FIG. 37, obturator 2700 is disposed within a cannula 2750. Cannula 2750 includes cannula tube 2752 extending distally from cannula housing 2754. Obturator housing 2710 is releasably coupled to cannula housing 2704. When obturator 2700 is coupled to cannula 2750, a portion of elongate shaft 2720 and member 2722 extend distally beyond distal end 2752*a* of cannula tube 2752. Each of the apertures (2726, 2728, and 2730) is positioned within cannula tube 2752 and proximal of distal end 2752*a* of cannula tube 2752.

Figure 38A:
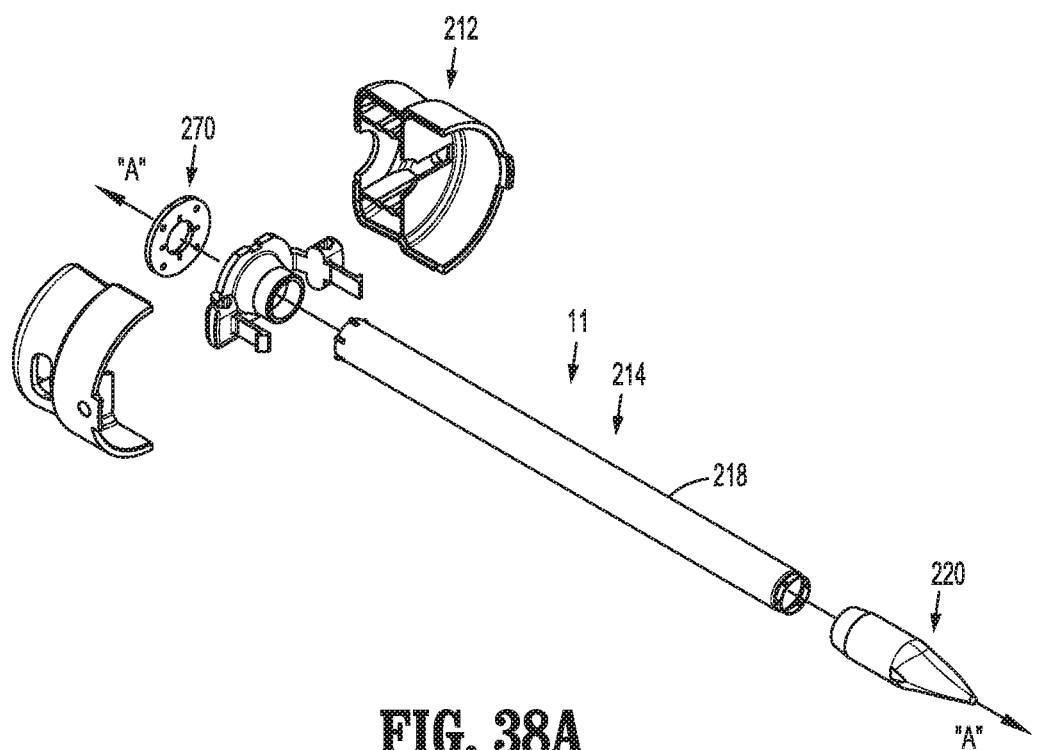
FIG. 38A is an exploded view of an obturator assembly, in accordance with an example embodiment of the present invention.
Figure 38B:
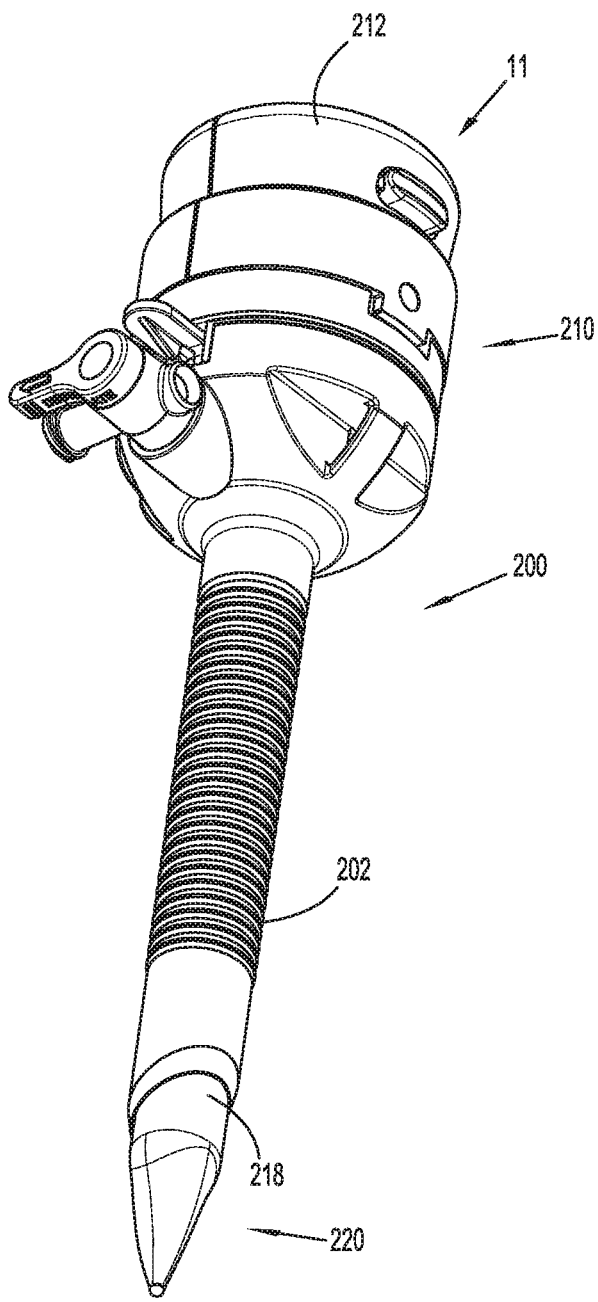
FIG. 38B is a perspective view of a surgical access system, with the obturator of FIG. 38A shown inserted therein, in accordance with an embodiment of the present invention.
Figure 39:
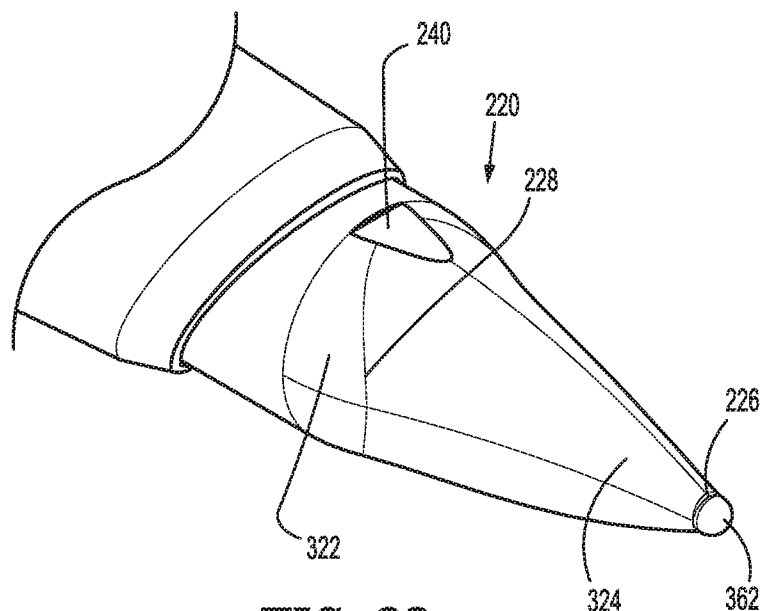
FIG. 39 is a perspective view of a distal end of the surgical access system of FIG. 38B.

FIGS. 38A-45 illustrate still another embodiment of the present invention. FIG. 38A is an exploded view of an obturator assembly 11, in accordance with an example embodiment of the present invention. FIG. 38B is a perspective view of a surgical access system 10 in which such an obturator is employed. In this embodiment, the obturator is an example of a bladeless optical obturator, which allows visualization during entry via an endoscope inserted into the obturator.

In this embodiment, the system 10 includes an obturator assembly 11 and a cannula assembly 200 which at least partially receives the obturator assembly 11. The obturator assembly 11 includes an obturator housing 212 disposed in mechanical cooperation with an elongated obturator member 214, and defines a longitudinal axis "A-A." The elongated obturator member 214 extends distally from the obturator housing 212.

The obturator member 214 includes an obturator shaft 218 mechanically coupled to the obturator housing 212, and an optical member 220 at the distal end of the obturator shaft 218. The obturator shaft 218 is made from either steel or a polymeric material. The optical member 220, which includes a hollow interior, includes a proximal section 322, a central section 324, and an atraumatic guiding nub 226. In use, a distal viewing tip of an endoscope is brought into engagement with a sloped surface 301 (FIGS. 43B and 43C) within the optical member 220, as will be described hereinbelow. An imaginary line 228 (shown to illustrate curvature) delineates the boundary between the proximal section 322 and the central section 324.

Figure 40:
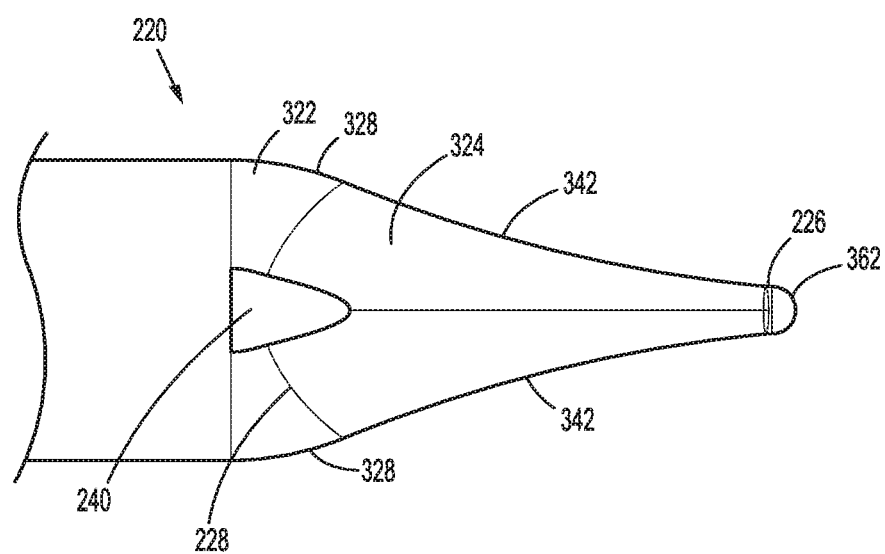
FIG. 40 is a top view of a distal end of the obturator of FIG. 38B.

With reference to FIG. 40, a top view of the optical member 220 is illustrated. As depicted, the proximal section 322 includes a pair of diametrically opposed convex surfaces 328, and the central section 324 includes a pair of diametrically opposed concave surfaces 342. The atraumatic guiding nub 226 extends distally from the central section 324 and includes a rounded end 362. The rounded end 362 defines a radius of curvature dimensioned to be atraumatic to tissue. The guiding nub 226 and the rounded end 362 are discussed in further detail hereinafter.

Figure 41:
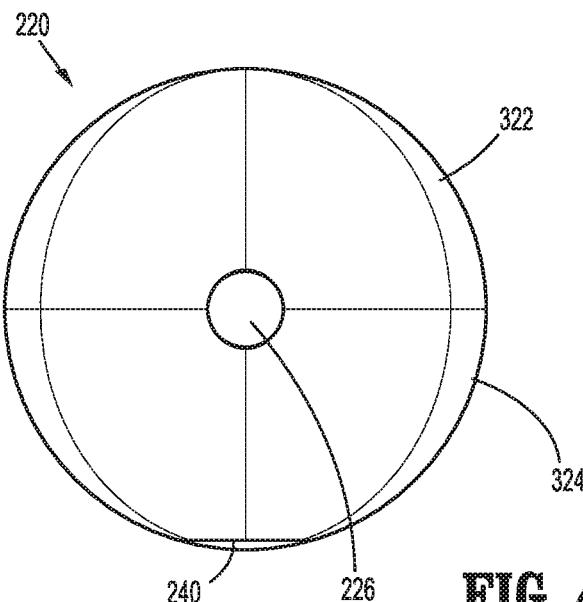
FIG. 41 is a front view of the distal end of the obturator of FIG. 38B.

With reference to FIG. 41, an end or axial view of the optical member 220 illustrates the circular profile of the rounded end 362, the reduced profile of the central section 324, and the circular profile of the proximal section 322.

Figure 42:
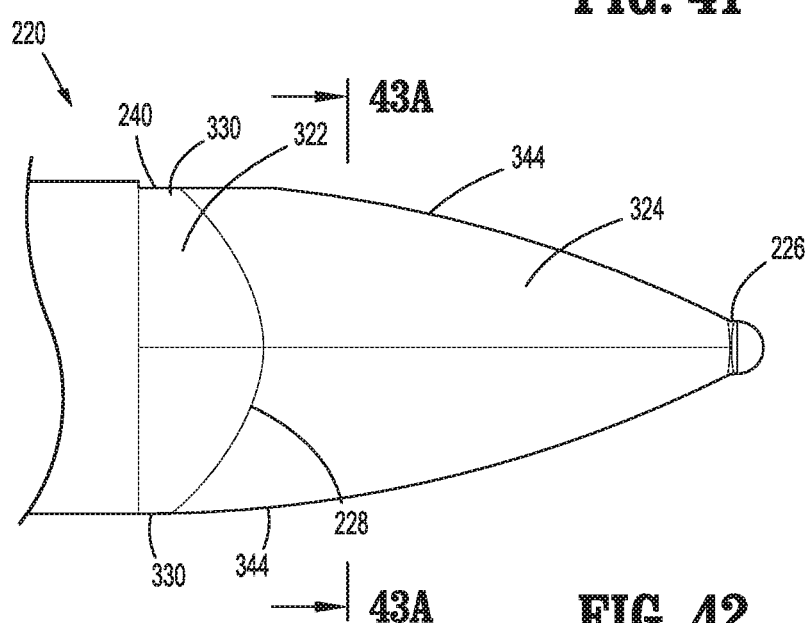
FIG. 42 is a side view of the distal end of the obturator of FIG. 38B.

With reference to FIG. 42, a side view of the optical member 220 is illustrated. This side view is radially offset 90° relative to the top view of FIG. 41. As shown, the proximal section 322 of the optical member 220 further includes a pair of diametrically opposed outer surfaces 330 which are generally linear and/or convex. The central section 324 also includes a pair of opposed outer surfaces 344 which are convex. Thus, the central section 324 of the optical member 220 is inclusive of both concave surfaces 342 (FIG. 40) and convex surfaces 344 (FIG. 42).

Figure 43A:
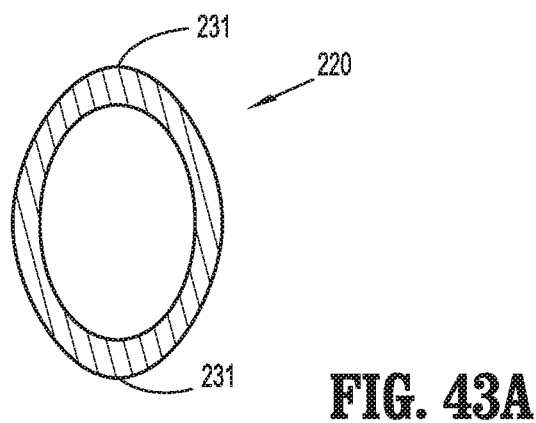
FIG. 43A is a cross-sectional view of the distal end of the obturator of FIG. 38B, taken at approximately the longitudinal midpoint thereof.

FIG. 43A is a cross-sectional view of the optical member 220 taken at approximately the longitudinal midpoint thereof. The figure illustrates that the optical member 220 includes rounded outer surfaces 231 that function to help separate tissue along the natural tissue planes.

The atraumatic guiding nub 226 permits initial insertion within an opening, e.g., a pre-cut scalpel incision, in the tissue and facilitates the advancement of the optical member 220 between the tissue layers to gently dissect tissue, without any cutting or incising of the tissue. After initial insertion and continued distal insertion, the central section 324 and the proximal portion 322 continue to gently enlarge the opening in tissue.

Figure 43B:
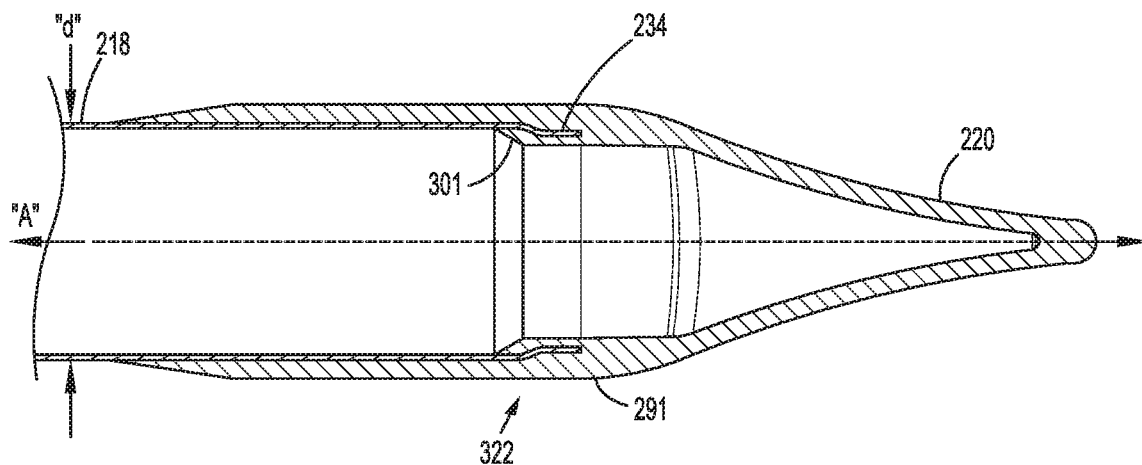
FIG. 43B is a top cross-sectional view of the distal end of the obturator of FIG. 38B.
Figure 43C:
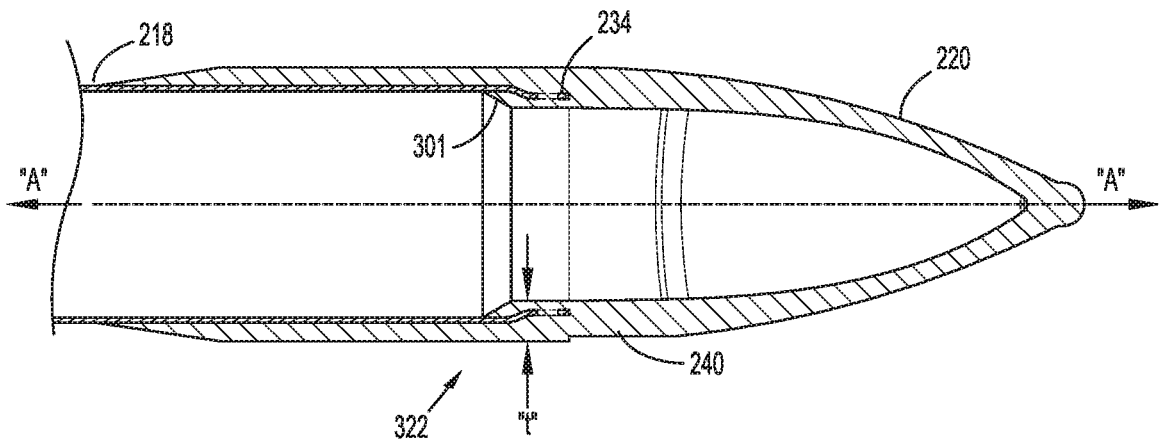
FIG. 43C is a side cross-sectional view of the distal end of the obturator of FIG. 38B.
Figure 43D:
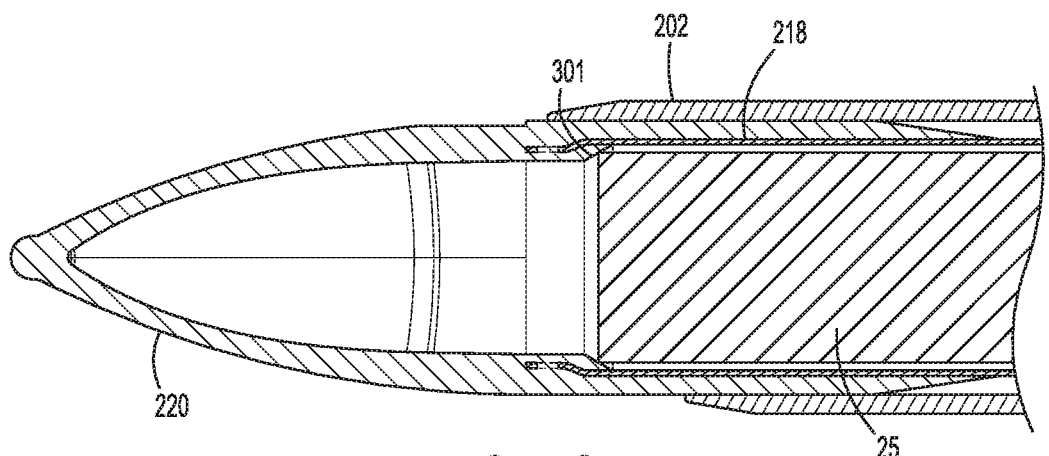
FIG. 43D is a side cross-sectional view of the distal end of the surgical access system of FIG. 38.

With reference to FIGS. 43B and 43C, the optical member 220 may be fabricated from a polymeric or thermoplastic material, and may be transparent or translucent to permit passage of light rays. During assembly, the optical member 220 is overmolded onto a radially outward flared portion 234 of the obturator shaft 218 to connect the components. The overmolded optical member 220 encapsulates flared portion 234.

The optical member 220 defines an internal chamfered or sloped surface 301 which is obliquely arranged relative to the longitudinal axis "A-A." The chamfered surface 301 is directly engaged by the outermost periphery of the distal end of the endoscope 25 (see FIG. 43D) such that light is transmitted radially within the outer periphery of the endoscope 25 and travels across an air gap prior to being received by the chamfered or sloped surface 301. The optical member 220 permits the passage of light rays to enable viewing, with the endoscope 25, of tissue adjacent the optical member 220 during the insertion and/or advancement of the trocar assembly.

As shown above in FIG. 43D, the distal end of the endoscope 25 engages the tapered surface 301 between the proximal and distal ends of the tapered surface 301. The obturator shaft 218 is positioned in a lumen of the elongated portion 202 of the cannula assembly 200. When the distal end of the endoscope 25 is engaged with the tapered surface 301 and the obturator shaft 218 is seated in the elongated portion 202, the distal end of the endoscope 25 is positioned proximally of the distalmost end of the elongated portion 202 of cannula assembly 200 such that the distalmost end of the elongated portion 202 extends beyond the distal end of the endoscope 25.

Figure 43E:
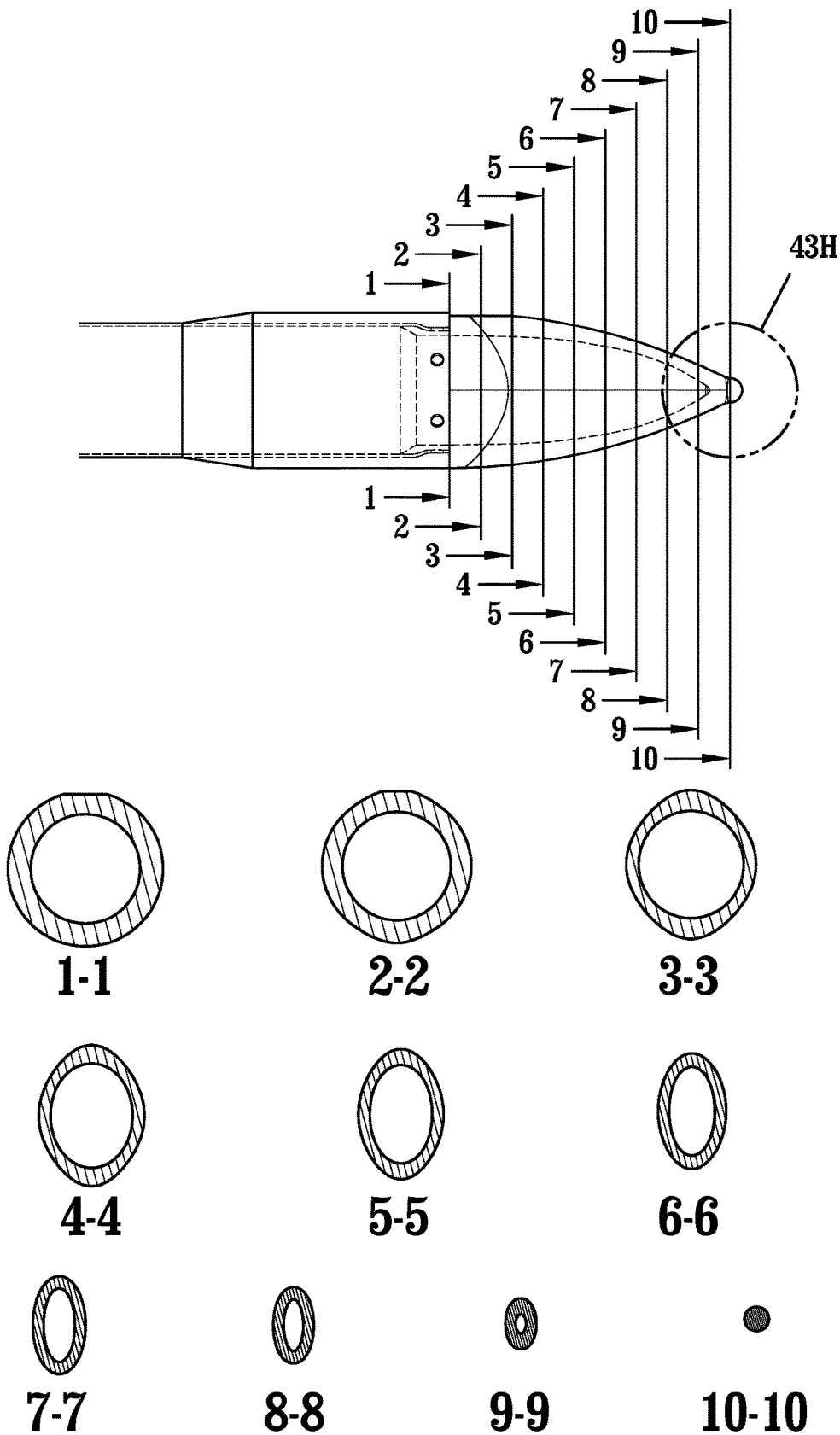
FIG. 43E is a side partial cross-sectional view of the distal end of the surgical access system of FIG. 38, including various cross-sectional views of the distal tip at various longitudinal positions.
Figure 43F:
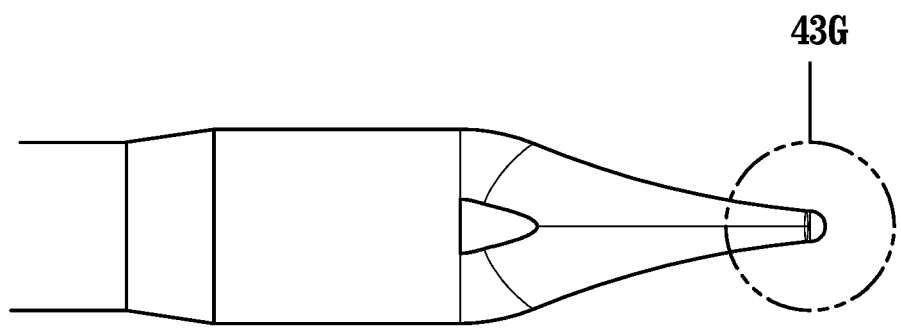

Referring to FIGS. 43E and 43F, a distal portion of the obturator assembly 11 including the optical member 220 is illustrated. The cross-sections taken along lines 1-1 and 2-2 through the proximal section 322 and flat surface 240 are substantially circular. The cross-sections taken along lines 3-3 and 4-4 through the central section 324 have a generally circular or irregular shape with pairs of diametrically opposed rounded outer surfaces 231. Cross-sections taken along lines 5-5, 6-6, 7-7, 8-8, and 9-9, through the central section 324 have a generally oval configuration. The cross-section taken along line 10-10 through the atraumatic guiding nub 226 of the optical member 220 is circular.

Figure 43G:
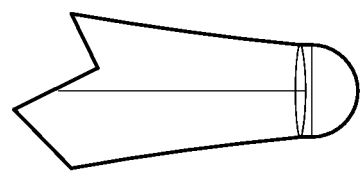
Figure 44:
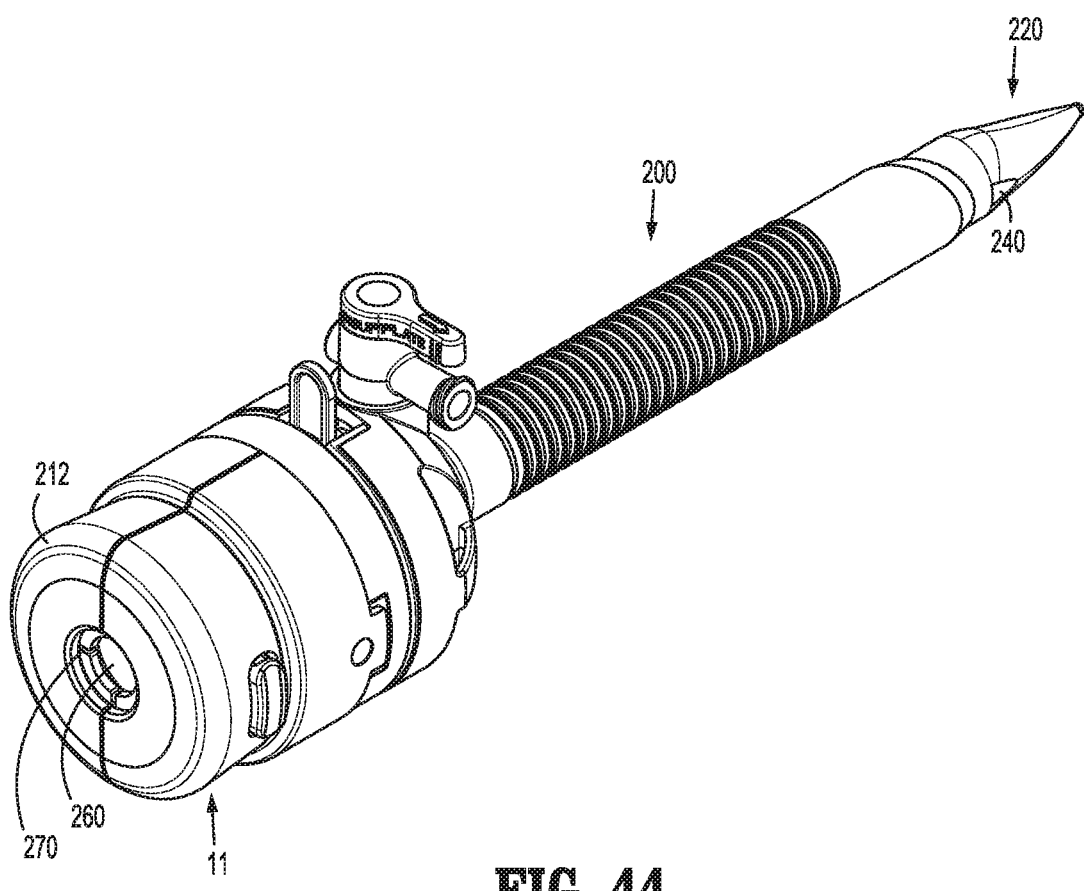
FIG. 44 is a rear perspective view of a surgical access system of FIG. 38B.
Figure 45A:
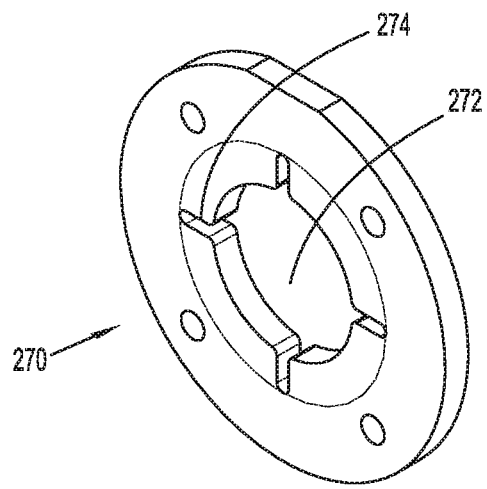
FIG. 45A is a perspective view of a flat elastomeric scope retention mechanism that may be fixed within the proximal housing of the obturator of FIG. 38, the scope retention mechanism depicted in a first configuration with slits.
Figure 45B:
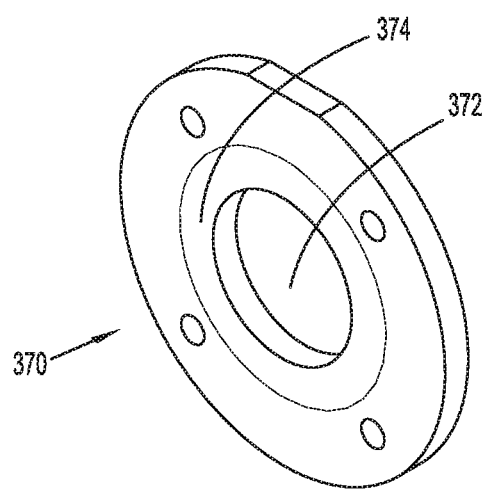
FIG. 45B is a perspective view of a flat elastomeric scope retention mechanism that may be fixed within the proximal housing of the obturator of FIG. 38, the scope retention mechanism depicted in a second configuration without slits.

Referring to FIGS. 43G and 43H, detailed views of the atraumatic guiding nub 226 are illustrated. As shown in FIG. 43H, the cross-sections taken along lines 11-11 and 12-12 through the atraumatic guiding nub 226 are circular with a constant diameter. The cross-section taken along line 13-13 through the central section 324 has a generally oval configuration.

The obturator member 214 is configured for insertion through the cannula assembly 200, as discussed above. The optical member 220 of the obturator assembly 11 is dimensioned such that an outer surface 291 of its proximal portion 322 provides a desired fit within the elongated portion 202 of the cannula assembly 200.

The obturator housing 212 of the obturator assembly 11 includes an opening 260 (FIG. 44) and a scope retention member 270 (FIG. 45A) adjacent the opening 260. The scope retention member 270 may be fabricated from an elastomeric material, and defines a central opening 272 for receiving the endoscope and four radial slits 274 extending outwardly from the central opening 272. The radial slits 274 permit flexure of the scope retention member 270 and enlargement of the central opening 272 upon insertion of the endoscope. The scope retention member 270 is adapted to engage the outer surface of the endoscope in frictional engagement therewith to assist in retaining the relative positioning of the endoscope within the obturator assembly 11 without locking the endoscope in position relative thereto.

In an alternative embodiment, a scope retention member 370 (FIG. 45B) is positioned adjacent the opening 260 of the obturator housing 212 of the obturator assembly 11. The scope retention member 370 may also be fabricated from an elastomeric material, and may define a central opening 372 for receiving the endoscope without any radial slits extending outwardly from the central opening 372. Instead, the central opening 372 is surrounded by a smooth surface 374 having an uninterrupted configuration (i.e., no slits or indentations). The scope retention member 370 is adapted to engage the outer surface of the endoscope in frictional engagement therewith to assist in retaining the relative positioning of the endoscope within the obturator assembly 11 without locking the endoscope in position relative thereto. The scope retention member 370 is capable of functioning as an instrument seal for a wider range of endoscopes or other instrumentation inserted through the central opening 372 (e.g., smaller scope or instrument sizes will also be sealed).

The use and function of system 10 will now be discussed in relation to FIG. 46. In embodiments, in laparoscopic surgery, the abdominal cavity is insufflated with a suitable biocompatible gas such as, e.g., $CO_2$ gas, to insufflate the body cavity and lift the body cavity wall away from the internal organs therein. The insufflation may be performed with an insufflation needle or similar device as is conventional in the art and/or the insufflation gas may be provided through the trocar assembly. In alternative embodiments, system 10 may also be utilized in a space that has not been insufflated.

In use, an initial incision "I" is made in tissue "T" (e.g., skin) by a surgical instrument (e.g., a scalpel). The incision "I" is preferably small, for example, within a range from about 2 mm to about 7 mm. Obturator assembly 11 of surgical access system 10 is at least partially introduced within cannula assembly 100 with obturator member extending through aperture 2166 of septum seal 2160 and through zero-closure seal 250 (see FIG. 6). The assembled unit is positioned within the initial incision and against the target tissue, e.g., the abdominal lining. An endoscope 411 may be inserted through obturator assembly 11 such that the distal viewing end of endoscope 411 is positioned against the chamfered surface of optical member 20. Endoscope 411 may be retained at this relative position within obturator assembly 11 by scope retention member 170.

During insertion, the tissue adjacent optical member 20 is viewed with endoscope 411. During advancement of system 10, endoscope 411 is utilized to view the path along which the system is advanced to ensure that any underlying tissue or organ site is prevented from contact with obturator assembly 11 and also to confirm entry within the body cavity.

Figure 46:
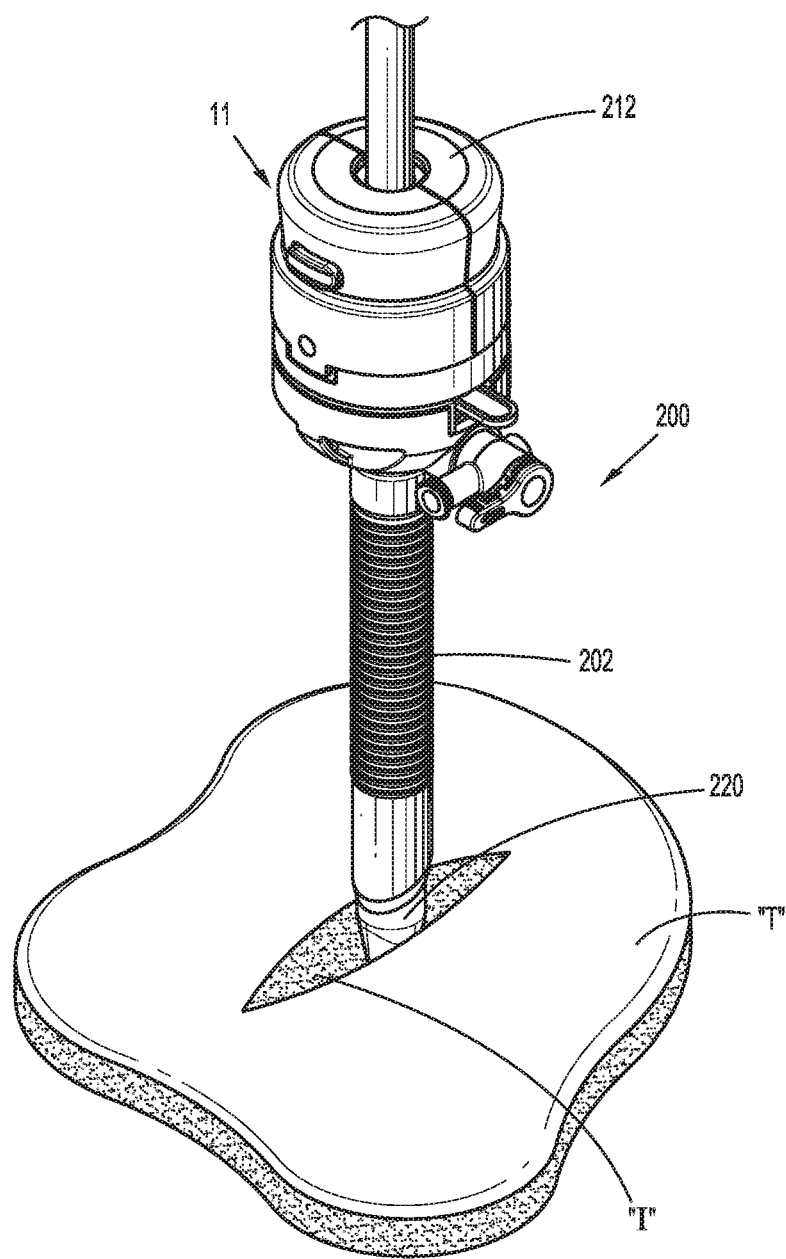
FIG. 46 is a perspective view of the surgical access system in use within an incision and having an endoscope inserted therein, in accordance with an embodiment of the present invention.

Once system 10 is positioned at the desired location, as shown in FIG. 46, endoscope 411 may be used to monitor the desired surgical procedure being performed within the cavity. Obturator assembly 11 may then be removed from cannula assembly 100. Instruments, such the same endoscope of various other types of instruments, may be introduced within cannula assembly 100 to perform a surgical procedure.

While various embodiments of the present disclosure have been shown and described herein, it will be obvious to those skilled in the art that these embodiments are provided by way of example only. Numerous variations, changes, and substitutions will now occur to those skilled in the art without departing from the present disclosure. Accordingly, it is intended that the invention be limited only by the spirit and scope of the appended claims.

The invention claimed is:
1. A valve assembly comprising:
a septum seal including an orifice configured to sealingly engage a surgical instrument inserted through the septum seal;
a first guard member positioned adjacent the septum seal, the first guard member including a plurality of first guard portions defining slits therebetween, wherein each slit progressively increases in width as each slit extends radially outward from a center aperture such that each slit is generally triangular in shape; and
a second guard member positioned adjacent to and in a radial offset position relative to the first guard member, the second guard member including a plurality of second guard portions defining slits therebetween, wherein each slit progressively increases in width as each slit extends radially outward from a center aperture such that each slit is generally triangular in shape.
2. The valve assembly of claim 1, wherein the slits of the first guard member align with the second guard portions, and the slits of the second guard member align with the first guard portions.

3. The valve assembly of claim 1, wherein the first and second guard members include respective flat guard portions, one or more of the slits extending from the respective center apertures to the flat guard portion.

4. The valve assembly of claim 3, wherein each slit extends radially beyond the plurality of respective first and second guard portions.

5. The valve assembly of claim 1, wherein the septum seal includes a bellows.

6. The valve assembly of claim 1, wherein the first and second guard members are disposed on a first side of the septum seal.

7. The valve assembly of claim 6, further comprising a third guard member and a fourth guard member, the third and fourth guard members being disposed on a second side of the septum seal.

8. The valve assembly of claim 1, wherein the pluralities of first and second guard portions are curved.

9. The valve assembly of claim 8, wherein each of the first and second guard members includes a flat guard portion, the plurality of first guard portions being secured to the flat guard portion of the first guard member and the plurality of second guard portions being secured to the flat guard portion of the second guard member.

10. The valve assembly of claim 1, further comprising an upper seal support and a lower seal support, the septum seal and the first and second guard members being retained between the upper and lower seal supports.

11. A valve assembly comprising:
a septum seal including an orifice configured to sealingly engage a surgical instrument inserted through the septum seal;
a first guard member positioned adjacent the septum seal, the first guard member including a plurality of first guard portions defining a first central aperture and a slit between adjacent first guard portions of the plurality of first guard portions, wherein each slit includes a width that progressively increases as each slit extends radially outward from the first central aperture; and
a second guard member positioned in an offset position relative to the first guard member, the second guard member including a plurality of second guard portions defining a second central aperture and a slit between adjacent second guard portions of the plurality of second guard portions, wherein each slit includes a width that progressively increases as each slit extends radially outward from the second central aperture.

12. The valve assembly of claim 11, wherein the slits of the first guard member align with the guard portions of the second guard member, and the slits of the second guard member align with the guard portions of the first guard member.

13. The valve assembly of claim 11, wherein the first and second guard members each include flat guard portions, one or more of the slits extending from the respective first and second central apertures to the respective flat guard portions.

14. The valve assembly of claim 13, wherein each slit extends radially beyond the plurality of respective first and second guard portions.

15. The valve assembly of claim 11, wherein the septum seal includes a bellows.

16. The valve assembly of claim 11, wherein the first and second guard members are disposed on a first side of the septum seal.

17. The valve assembly of claim 16, further comprising a third guard member and a fourth guard member, the third and fourth guard members being disposed on a second side of the septum seal.

18. The valve assembly of claim 11, wherein the pluralities of first and second guard portions are curved.

19. The valve assembly of claim 18, wherein each of the first and second guard members includes a flat guard portion, the plurality of first guard portions being secured to the flat guard portion of the first guard member and the plurality of second guard portions being secured to the flat guard portion of the second guard member.

20. The valve assembly of claim 11, further comprising an upper seal support and a lower seal support, the septum seal and the first and second guard members being retained between the upper and lower seal supports.

* * * * *